US011767367B2

(12) United States Patent
Arlen et al.

(10) Patent No.: US 11,767,367 B2
(45) Date of Patent: Sep. 26, 2023

(54) MONOCLONAL ANTIBODY NEO-201 FOR THE TREATMENT OF HUMAN CARCINOMAS

(71) Applicant: PRECISION BIOLOGICS, INC., Bethesda, MD (US)

(72) Inventors: Philip M. Arlen, Rockville, MD (US); Kwong Y. Tsang, Bethesda, MD (US)

(73) Assignee: PRECISION BIOLOGICS, INC., Bethesda, MD (US)

( * ) Notice: Subject to any disclaimer, the term of this patent is extended or adjusted under 35 U.S.C. 154(b) by 209 days.

(21) Appl. No.: 16/761,404

(22) PCT Filed: Nov. 2, 2018

(86) PCT No.: PCT/US2018/059039
§ 371 (c)(1),
(2) Date: May 4, 2020

(87) PCT Pub. No.: WO2019/090134
PCT Pub. Date: May 9, 2019

(65) Prior Publication Data
US 2020/0362053 A1 Nov. 19, 2020

Related U.S. Application Data

(60) Provisional application No. 62/592,778, filed on Nov. 30, 2017, provisional application No. 62/581,380, filed on Nov. 3, 2017.

(51) Int. Cl.
| | | |
|---|---|---|
| *C07K 16/30* | (2006.01) | |
| *A61P 35/00* | (2006.01) | |
| *A61K 39/395* | (2006.01) | |
| *A61K 45/06* | (2006.01) | |
| *A61K 39/00* | (2006.01) | |

(52) U.S. Cl.
CPC ........ *C07K 16/30* (2013.01); *A61K 39/39558* (2013.01); *A61K 45/06* (2013.01); *A61P 35/00* (2018.01); *A61K 2039/505* (2013.01); *C07K 2317/21* (2013.01); *C07K 2317/24* (2013.01); *C07K 2317/732* (2013.01); *C07K 2317/734* (2013.01)

(58) Field of Classification Search
CPC combination set(s) only.
See application file for complete search history.

(56) References Cited

U.S. PATENT DOCUMENTS

2013/0189268 A1  7/2013 Du et al.

FOREIGN PATENT DOCUMENTS

| | | | |
|---|---|---|---|
| JP | 2017-521410 T | 8/2017 | |
| WO | 2014106176 | 7/2014 | |
| WO | WO-2018218230 A1 * | 11/2018 | ......... A61K 39/0011 |

OTHER PUBLICATIONS

Arlen 2017 (The Discovery and Development of Novel Monoclonal Antibodies Targeting Neoantigens, Precision Biologics Feb. 2017). (Year: 2017).*
Van Audenaerde et al (Interleukin-15 stimulates natural killer cell-mediated killing of both human pancreatic cancer and stellate cells, Oncotarget, vol. 8, May 2017) (Year: 2017).*
Neuman et al (2016) Identification of target and cytotoxicity of novel and monoclonal antibody NEO-201 in ovarian and uterine cancer subtypes, Gynecologic Oncology, vol. 141, Jun. 2016). (Year: 2016).*
Fantini et al. "Preclinical characterization of a novel monoclonal antibody NEO-201 for the treatment of human carcinomas." Frontiers in immunology. Jan. 4, 2018;8:1899.
Zeligs K, Arlen PM, Tsang K, Hernandez L, Fantini M, Annunziata CM. Preclinical characterization of a novel monoclonal antibody targeting a neo-antigen expressed in ovarian and GI malignancies. Cancer Research. Jul. 1, 2017;77(13_Supplement):3025-.
Neuman MK, Hernandez L, Wang XP, Saric O, Dubeykovskiy A, Arlen P, Annunziata CM. Identification of target and cytotoxicity of novel monoclonal antibody NEO-201 in ovarian and uterine cancer subtypes. Cancer Research. Jul. 15, 2016;76(14_Supplement):1496-.
Geisler, J.P. et al., "231-Poster, CA-125 and grade 1 endometrial cancer: Analyzing the risk of metastases." Gynecol Oncol, 2016,vol. 141,p. 95-96.
Vidarsson G, Dekkers G, Rispens T. IgG subclasses and allotypes: from structure to effector functions. Frontiers in immunology. Oct. 20, 2014;5:520: pp. 1-17.
Zeligs K, Arlen PM, Tsang K, Hernandez L, Fantini M, Annunziata CM. Predinical characterization of a novel monoclonal antibody targeting a neo-antigen expressed in ovarian and GI malignancies. Cancer Research. Jul. 1, 2017;77(13_Supplement):3025-.

* cited by examiner

*Primary Examiner* — Laura B Goddard
*Assistant Examiner* — Sarah A Alsomairy
(74) *Attorney, Agent, or Firm* — Robin L. Teskin; Baker, Donelson, Bearman, Caldwell & Berkowitz PC

(57) ABSTRACT

NEO-201 is a humanized IgG1 monoclonal antibody (mAb) that is highly reactive against the majority of tumor tissues from many different carcinomas, including colon, pancreatic, stomach, lung, breast, and uterine cancers, but the overwhelming majority of normal tissues are not recognized by this antibody. Functional assays revealed that NEO-201 is capable of mediating both antibody-dependent cellular cytotoxicity (ADCC) and complement-dependent cytotoxicity (CDC) against tumor cells. Furthermore, the growth of human pancreatic xenograft tumors in vivo was largely attenuated by treatment with NEO-201 both alone and in combination with human peripheral blood mononuclear cells (PBMC) as an effector cell source for ADCC. In vivo biodistribution studies in human tumor xenograft-bearing mice revealed that NEO-201 preferentially accumulates in the tumor but not organ tissue. A single-dose toxicity study in non-human primates demonstrated safety and tolerability of NEO-201, as a transient decrease in circulating neutrophils was the only related adverse effect observed.

19 Claims, 13 Drawing Sheets

Specification includes a Sequence Listing.

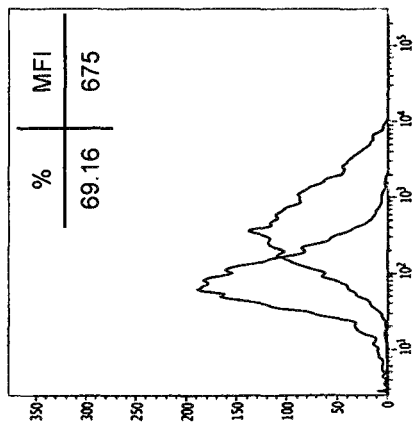
FIG. 1A High – CFPAC-1
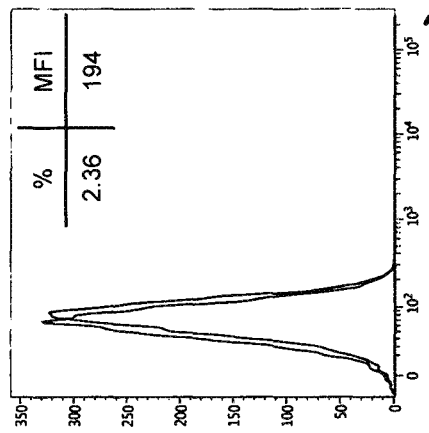
FIG. 1B Medium – H441
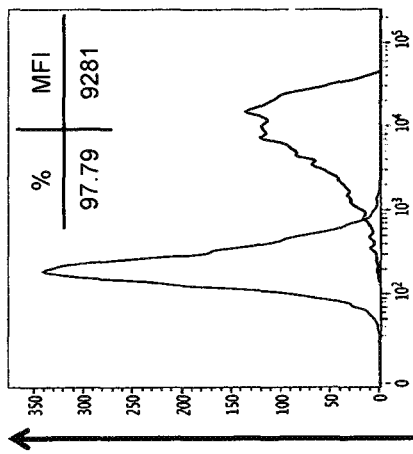
FIG. 1C Low – HCC1937
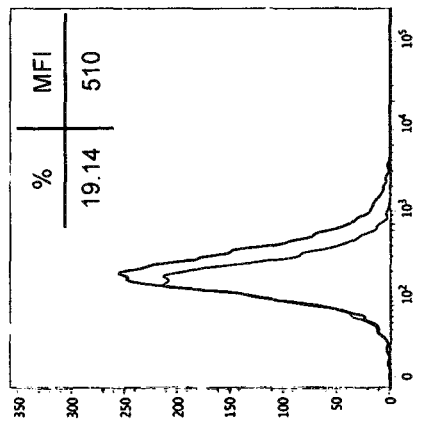
FIG. 1D Negative – SW1116
NEO-201

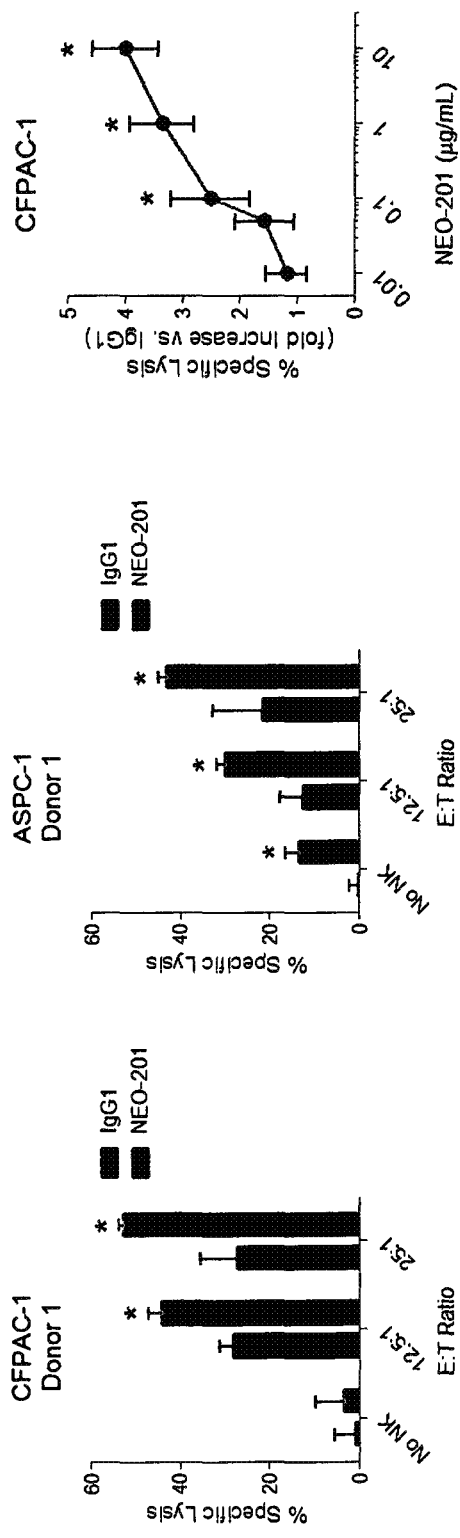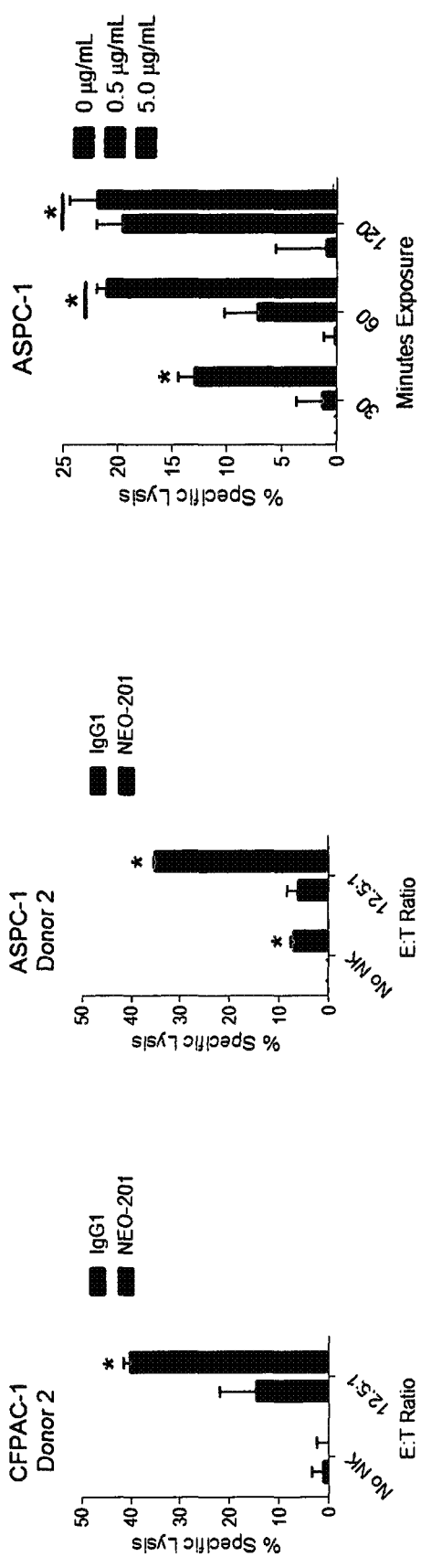
FIG. 3A
FIG. 3B
FIG. 3C

FIG. 8. Treatment with ALT-803 enhance ADCC activity mediated by NEO-201

| | ALT-803 (25ng/ml) | Antibody (10µg/ml) | E:T = 25:1 | E:T = 12.5:1 | E:T = 6.25:1 |
|---|---|---|---|---|---|
| ND#1 | - | NEO-201 | 19.4 (0.9) | ND | ND |
| ND#1 | + | NEO-201 | 30.3 (1.3) | ND | ND |
| ND#2 | - | NEO-201 | 69.1 (1.9) | 47.6 (1.5) | 29.3 (1.0) |
| ND#2 | + | NEO-201 | 87.6 (2.8) | 79.0 (1.6) | 65.1 (2.8) |

FIG. 9  Treatment with ALT-803 enhanced the expression of TIM-3 and NKG2D on human NK cells

| Markers | Untreated | Treated with ALT-803 48h (25ng/ml) |
|---|---|---|
| CD16-/CD56+ | 9.51 (52/3,457) | 9.03 (84/15,419) |
| CD16+/CD56+ | 89.27 (7,434/1,048) | 90.97 (6,915/3,605) |
| TIM-3+/CD16+/CD56+ | 42.87 (843/8,078/1,197) | 81.56 (2,972/6,039/2,820) |
| NKG2D+/CD16+/CD56+ | 87.99 (317/7,341/1,070) | 78.33 (590/5,829/2,463) |
| TIM-3+/NKG2D+/CD16+/CD56+ | 43.95 (799/307/8,028/1,204) | 74.68 (3,011/500/6,123/2,937) |
| CD107a+/CD16+/CD56+ | 99.99 (887/7,439/1,050) | 99.91 (2,711/5,739/2,305) |
| Granzyme B+/CD16+/CD56+ | 98.84 (474/7,512/1,045) | 99.88 (1,346/5,743/2,305) |
| PD-1+/CD16+/CD56+ | 12.82 (907/3,770/532) | 16.18 (1,272/4,749/674) |
| CD158d+/CD16+/CD56+ | 14.58 (167/6,302/2,654) | 17.68 (1,064/2,951/3,237) |

FIG. 10. Treatment with ALT-803 enhanced the expression of TIM-3 and NKG2D on human NK cells

| Markers | Untreated | Treated with ALT-803 48h (25ng/ml) |
|---|---|---|
| CD16-/CD56+ | 12.27 (83/908) | 13.23 (91/757) |
| CD16+/CD56+ | 87.73 (6,425/3,043) | 86.77 (5,848/7,810) |
| TIM-3+/CD16+/CD56+ | 33.92 (827/6,901/3,040) | 92.14 (2,462/5,903/8,080) |
| NKG2D+/CD16+/CD56+ | 79.46 (465/6,444/3,094) | 95.40 (1,152/5,939/8,074) |
| TIM-3+/NKG2D+/CD16+/CD56+ | 24.85 (853/511/6,925/3,117) | 85.30 (2,517/1,190/6,051/8,385) |
| CD107a+/CD16+/CD56+ | 99.95 (13,775/6,425/3,043) | 100 (10,365/5,848/7,810) |
| Granzyme B+/CD16+/CD56+ | 99.75 (1,157/6,430/3,042) | 100 (2,457/5,848/7,810) |
| PD-1+/CD16+/CD56+ | 5.36 (211/7,113/3,278) | 3.87 (229/5,976/5,872) |
| CD158d+/CD16+/CD56+ | 12.72 (227/19,155/4,833) | 11.00 (219/9,661/8,955) |

FIG. 11. Treatment with ALT-803 enhance ADCC activity mediated by low concentrations NEO-201

| Antibody | ALT-803 (25ng/ml) | Antibody (10µg/ml) | Antibody (1µg/ml) | Antibody (0.1µg/ml) |
|---|---|---|---|---|
| NEO-201 | - | 23.8 (1.7) | 24.8 (1.3) | 14.9 (2.9) |
| NEO-201 | + | 37.3 (1.5)* | 37.4 (1.3)* | 37.4 (1.5)* |

FIG. 12. Treatment with ALT-803 enhance ADCC activity of a normal donor (ND#8) with minimal ADCC activity mediated by and NEO-201 and the activity can be blocked by anti-CD16 and anti-TIM-3 antibody

| ALT-803 (25ng/ml) | None | Anti-CD16 (30µg/ml) | Anti-CD16 (15µg/ml) | Anti-TIM-3 (30µg/ml) | Anti-TIM-3 (15µg/ml) |
|---|---|---|---|---|---|
| - | 1.3 (1.4) | 0.1 (1.9) | 1.8 (2.5) | 3.2 (2.5) | 0.6 (2.2) |
| + | 12.3 (1.1)* | 4.4 (0.9)# | 6.3 (2.3)# | 5.7 (2.7)# | 13.5 (1.9) |

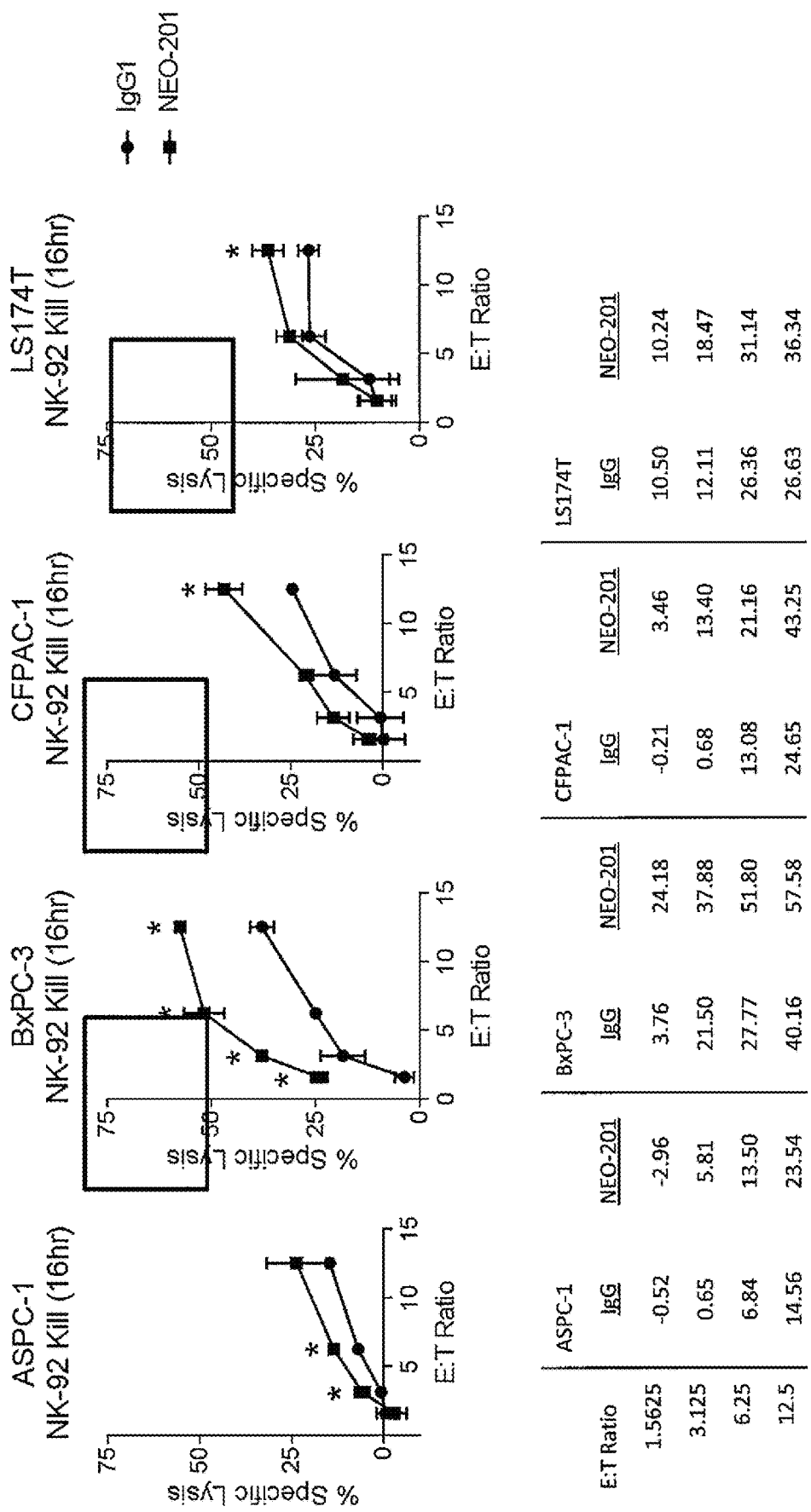

SEQUENCE LISTING

<160> NUMBER OF SEQ ID NOS: 39

<210> SEQ ID NO 1
<211> LENGTH: 11
<212> TYPE: PRT
<213> ORGANISM: Mus musculus

<400> SEQUENCE: 1

Gly Ala Ser Glu Asn Ile Tyr Gly Ala Leu Asn
1               5                   10

<210> SEQ ID NO 2
<211> LENGTH: 7
<212> TYPE: PRT
<213> ORGANISM: Mus musculus

<400> SEQUENCE: 2

Gly Ala Ser Asn Leu Ala Asp
1               5

```
<210> SEQ ID NO 3
<211> LENGTH: 9
<212> TYPE: PRT
<213> ORGANISM: Mus musculus

<400> SEQUENCE: 3

Gln Asn Val Leu Ser Ser Pro Tyr Thr
1               5

<210> SEQ ID NO 4
<211> LENGTH: 11
<212> TYPE: PRT
<213> ORGANISM: Homo sapiens

<400> SEQUENCE: 4

Gln Ala Ser Glu Asn Ile Tyr Gly Ala Leu Asn
1               5                   10

<210> SEQ ID NO 5
<211> LENGTH: 7
<212> TYPE: PRT
<213> ORGANISM: Homo sapiens

<400> SEQUENCE: 5

Gly Ala Ser Asn Leu Ala Thr
1               5

<210> SEQ ID NO 6
<211> LENGTH: 9
<212> TYPE: PRT
<213> ORGANISM: Homo sapiens

<400> SEQUENCE: 6

Gln Gln Val Leu Ser Ser Pro Tyr Thr
1               5

<210> SEQ ID NO 7
<211> LENGTH: 10
<212> TYPE: PRT
<213> ORGANISM: Mus musculus

<400> SEQUENCE: 7

Gly Tyr Thr Phe Thr Asp Tyr Ala Met His
1               5                   10

<210> SEQ ID NO 8
<211> LENGTH: 17
<212> TYPE: PRT
<213> ORGANISM: Mus musculus

<400> SEQUENCE: 8

Leu Ile Ser Thr Tyr Ser Gly Asp Thr Lys Tyr Asn Gln Asn Phe Lys
1               5                   10                  15

Gly

<210> SEQ ID NO 9
<211> LENGTH: 12
<212> TYPE: PRT
<213> ORGANISM: Mus musculus

<400> SEQUENCE: 9

Gly Asp Tyr Ser Gly Ser Arg Tyr Trp Phe Ala Tyr
1               5                   10
```

<210> SEQ ID NO 10
<211> LENGTH: 17
<212> TYPE: PRT
<213> ORGANISM: Homo sapiens

<400> SEQUENCE: 10

```
Leu Ile Ser Thr Tyr Ser Gly Asp Thr Lys Tyr Asn Gln Asn Phe Gln
1               5                   10                  15
Gly
```

<210> SEQ ID NO 11
<211> LENGTH: 12
<212> TYPE: PRT
<213> ORGANISM: Homo sapiens

<400> SEQUENCE: 11

```
Gly Asp Tyr Ser Gly Ser Arg Tyr Trp Phe Ala Tyr
1               5                   10
```

<210> SEQ ID NO 12
<211> LENGTH: 965
<212> TYPE: DNA
<213> ORGANISM: Mus musculus

<400> SEQUENCE: 12

| | | | | | | |
|---|---|---|---|---|---|---|
| gcggggcagc | ctcacacaga | acacacacag | atatgggtgt | acccactcag | ctcctgttgc | 60 |
| tgtggcttac | agtcgtagtt | gtcagatgtg | acatccagat | gactcagtct | ccagcttcac | 120 |
| tgtctgcatc | tgtgggagaa | actgtcacca | tcacatgtgg | agcaagtgag | aatatttacg | 180 |
| gtgctttaaa | ttggtatcag | cggaaacagg | gaaaatctcc | tcagctcctg | atttatggcg | 240 |
| caagtaattt | ggcagatggc | atgtcatcga | ggttcagtgg | cagtggatct | ggtagacagt | 300 |
| attctctcaa | gatcagtagc | ctgcatcctg | acgatgttgc | aacgtattac | tgtcaaaatg | 360 |
| tattaagtag | tccgtacacg | ttcggagggg | ggaccaagct | ggaaataaaa | cgggctgatg | 420 |
| ctgcaccaac | tgtatccatc | ttcccaccat | ccagtgagca | gttaacatct | ggaggtgcct | 480 |
| cagtcgtgtg | cttcttgaac | aacttctacc | ccaaagacat | caatgtcaag | tggaagattg | 540 |
| atggcagtga | acgacaaaat | ggcgtcctga | acagttggac | tgatcaggac | agcaaagaca | 600 |
| gcacctacag | catgagcagc | accctcacgt | tgaccaagga | cgagtatgaa | cgacataaca | 660 |
| gctatacctg | tgaggccact | cacaagacac | aacttcacc | cattgtcaag | agcttcaaca | 720 |
| ggaatgagtt | ttagagacaa | aggtcctgag | acgccaccac | cagctcccca | gctccatcct | 780 |
| atcttcccctt | ctaaggtctt | ggaggcttcc | ccacaagcga | cctaccactg | ttgcggtgct | 840 |
| ccaaacctcc | tccccacctc | cttctcctcc | tcctcccttt | ccttggcttt | tatcatgcta | 900 |
| atatttgcag | aaaatattca | ataaagtgag | tctttgcaca | aaaaaaaaa | aaaaaaaaa | 960 |
| aaaaa | | | | | | 965 |

<210> SEQ ID NO 13
<211> LENGTH: 1575
<212> TYPE: DNA
<213> ORGANISM: Mus musculus

<400> SEQUENCE: 13

| | | | | | | |
|---|---|---|---|---|---|---|
| acgcgggaca | cagtagtctc | tacagtcaca | ggagtacaca | ggacattgcc | atgggttgga | 60 |
| gctgtatcat | cttctttctg | gtagcaacag | ctacaggtgt | gcactcccag | gtccagctgc | 120 |
| agcagtctgg | gcctgaggtg | gtgaggcctg | ggtctcagt | gaagatttcc | tgcaagggtt | 180 |

```
ccggctacac attcactgat tatgctatgc actgggtgaa gcagagtcat gcaaagagtc    240
tcgagtggat tggacttatt agtacttaca gtggtgatac aaagtacaac cagaacttta    300
agggcaaggc cacaatgact gtagacaaat cctccaacac agcctatatg aacttgcca     360 gattgacatc tgaggattct gccatctatt actgtgcaag aggggattat ccggtagta     420 ggtactggtt tgcttactgg ggccaaggga ctctggtcac tgtctctgca gccaaaacga    480
cacccccatc tgtctatcca ctggcccctg gatctgctgc ccaaactaac tccatggtga    540
ccctgggatg cctggtcaag ggctatttcc ctgagccagt gacagtgacc tggaactctg    600
gatccctgtc cagcggtgtg cacaccttcc cagctgtcct gcagtctgac tctacactc     660 tgagcagctc agtgactgtc cctccagca cctggcccag cgagaccgtc acctgcaacg     720
ttgcccaccc ggccagcagc accaaggtgg acaagaaaat tgtgcccagg gattgtggtt    780
gtaagccttg catatgtaca gtcccagaag tatcatctgt cttcatcttc ccccaaagc     840 ccaaggatgt gctcaccatt actctgactc taaggtcac gtgtgttgtg gtagacatca     900
gcaaggatga tcccgaggtc cagttcagct ggtttgtaga tgatgtggag gtgcacacag     960
ctcagacgca accccgggag gagcagttca acagcacttt ccgctcagtc agtgaacttc    1020
ccatcatgca ccaggactgg ctcaatggca aggagttcaa atgcagggtc aacagtgcag    1080
cttttccctg ccccatcgag aaaaccatct ccaaaaccaa aggcagaccg aaggctccac    1140
aggtgtacac cattccacct cccaaggagc agatggccaa ggataaagtc agtctgacct    1200
gcatgataac agacttcttc cctgaagaca ttactgtgga gtggcagtgg aatgggcagc    1260
cagcggagaa ctacaagaac actcagccca tcatggacac agatggctct tacttcgtct    1320
acagcaagct caatgtgcag aagagcaact gggaggcagg aaatactttc acctgctctg    1380
tgttacatga gggcctgcac aaccaccata ctgagaagag cctctcccac tctcctggta    1440
aatgatccca gtgtccttgg agccctctgg ccctacagga ctttgacacc tacctccacc    1500
cctccctgta taaataaagc acccagcact gcctcgggac cctgcataaa aaaaaaaaa    1560 aaaaaaaaaa aaaaa                                                       1575
```

<210> SEQ ID NO 14
<211> LENGTH: 107
<212> TYPE: PRT
<213> ORGANISM: Mus musculus

<400> SEQUENCE: 14

Leu Met Thr Gln Ser Pro Ala Ser Leu Ser Ala Ser Val Gly Glu Thr
1               5                   10                  15

Val Thr Ile Thr Cys Gly Ala Ser Glu Asn Ile Tyr Gly Ala Leu Asn
            20                  25                  30

Trp Tyr Gln Arg Lys Gln Gly Lys Ser Pro Gln Leu Leu Ile Tyr Gly
        35                  40                  45

Ala Ser Asn Leu Ala Asp Gly Met Ser Ser Arg Phe Ser Gly Ser Gly
    50                  55                  60

Ser Gly Arg Gln Tyr Ser Leu Lys Ile Ser Ser Leu His Pro Asp Asp
65                  70                  75                  80

Val Ala Thr Tyr Tyr Cys Gln Asn Val Leu Ser Pro Tyr Thr Phe
                85                  90                  95

Gly Gly Gly Thr Lys Leu Glu Ile Lys Lys Gly
            100                 105

```
<210> SEQ ID NO 15
<211> LENGTH: 116
<212> TYPE: PRT
<213> ORGANISM: Mus musculus

<400> SEQUENCE: 15

Leu Glu Glu Ser Gly Pro Glu Val Val Arg Pro Gly Val Ser Val Lys
1               5                   10                  15

Ile Ser Cys Lys Gly Ser Gly Tyr Thr Phe Thr Asp Tyr Ala Met His
            20                  25                  30

Trp Val Lys Gln Ser His Ala Lys Ser Leu Glu Trp Ile Gly Leu Ile
        35                  40                  45

Ser Thr Tyr Ser Gly Asp Thr Lys Tyr Asn Gln Asn Phe Lys Gly Lys
    50                  55                  60

Ala Thr Met Thr Val Asp Lys Ser Ser Asn Thr Ala Tyr Met Glu Leu
65                  70                  75                  80

Ala Arg Leu Thr Ser Glu Asp Ser Ala Ile Tyr Tyr Cys Ala Arg Gly
                85                  90                  95

Asp Tyr Ser Gly Ser Arg Tyr Trp Phe Ala Tyr Trp Gly Gln Gly Thr
            100                 105                 110

Thr Val Thr Arg
        115

<210> SEQ ID NO 16
<211> LENGTH: 107
<212> TYPE: PRT
<213> ORGANISM: Mus musculus

<400> SEQUENCE: 16

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Ser Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45
```

```
Tyr Gly Ala Ser Asn Leu Ala Asp Gly Met Pro Ser Arg Phe Ser Gly
        50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
                100                 105
```

<210> SEQ ID NO 18
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Arg Lys Pro Gly Lys Ser Pro Lys Leu Leu Ile
            35                  40                  45

Tyr Gly Ala Ser Asn Leu Ala Asp Gly Met Pro Ser Arg Phe Ser Gly
        50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
                100                 105
```

<210> SEQ ID NO 19
<211> LENGTH: 107
<212> TYPE: PRT
<213> ORGANISM: Artificial sequence
<220> FEATURE:
<223> OTHER INFORMATION: Humanized antibody sequence

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
                20                  25                  30

Leu Asn Trp Tyr Gln Arg Lys Pro Gly Lys Ser Pro Lys Leu Leu Ile
            35                  40                  45

Tyr Gly Ala Ser Asn Leu Ala Thr Gly Met Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Ser Ser Pro Tyr
                85                  90                  95

Thr Phe Gly Gly Gly Thr Lys Leu Glu Ile Lys
                100                 105
```

<210> SEQ ID NO 20
<211> LENGTH: 107
<212> TYPE: PRT
<213> ORGANISM: Artificial sequence

```
<220> FEATURE:
<223> OTHER INFORMATION: Humanized antibody sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Arg Gln Tyr Thr Phe Thr Ile Ser Ser Leu Gln Pro
65              70                  75                  80

Glu Asp Ile Ala Thr Tyr Tyr Cys Gln Gln Val Leu Ser Ser Pro Tyr
            85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Asn Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65              70                  75                  80

Glu Asp Val Ala Thr Tyr Tyr Cys Gln Asn Val Leu Ser Ser Pro Tyr
            85                  90                  95

Thr Phe Gly Gly Gly Thr Lys Leu Glu Ile Lys
            100                 105

<210> SEQ ID NO 22
<211> LENGTH: 121
<212> TYPE: PRT
<213> ORGANISM: Mus musculus

<400> SEQUENCE: 22

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Ser Asn Thr Ala Tyr
65              70                  75                  80
```

```
Met Glu Leu Ala Arg Leu Thr Ser Glu Asp Ser Ala Ile Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ala
        115                 120

<210> SEQ ID NO 23
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Arg Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 24
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Thr Ser Ile Ser Thr Ala Tyr
65                  70                  75                  80

Met Glu Leu Ser Arg Leu Arg Ser Asp Asp Thr Ala Ile Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120
```

```
<210> SEQ ID NO 25
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Met
        35                  40                  45

Gly Leu Ile Ser Thr Tyr Ser Gly Asp Thr Lys Tyr Ser Gln Lys Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 26
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Ile
        35                  40                  45

Gly Leu Ile Ser Thr Tyr Ser Gly Asp Thr Lys Tyr Asn Gln Lys Phe
    50                  55                  60

Gln Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 27
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 27

Gln Val Gln Leu Val Gln Ser Gly Ala Glu Val Lys Lys Pro Gly Ala
1               5                   10                  15
```

Ser Val Lys Val Ser Cys Lys Gly Ser Gly Tyr Thr Phe Thr Asp Tyr
            20                  25                  30

Ala Met His Trp Val Arg Gln Val His Ala Gln Gly Leu Glu Trp Ile
        35                  40                  45

Gly Leu Ile Ser Thr Tyr Ser Gly Asp Thr Lys Tyr Asn Gln Asn Phe
 50                  55                  60

Lys Gly Lys Ala Thr Met Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 28
<211> LENGTH: 470
<212> TYPE: PRT
<213> ORGANISM: Artificial sequence
<220> FEATURE:
<223> OTHER INFORMATION: Humanized antibody sequence (h16C3-Abb* heavy
      chain)
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(140)
<223> OTHER INFORMATION: Variable region
<220> FEATURE:
<221> NAME/KEY: MISC_FEATURE
<222> LOCATION: (141)..(470)
<223> OTHER INFORMATION: Constant region
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (70)..(85)
<223> OTHER INFORMATION: CDR2
<220> FEATURE:
<221> NAME/KEY: MISC_FEATURE
<222> LOCATION: (118)..(129)
<223> OTHER INFORMATION: CDR3

<400> SEQUENCE: 28

Met Gly Trp Ser Cys Ile Ile Phe Phe Leu Val Ala Thr Ala Thr Gly
 1               5                  10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Arg Leu
 50                  55                  60

Glu Trp Met Gly Leu Ile Ser Thr Tyr Ser Gly Asp Thr Lys Tyr Asn
 65                  70                  75                  80

Gln Asn Phe Gln Gly Arg Val Thr Met Thr Val Asp Lys Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg Gly Asp Tyr Ser Gly Ser Arg Tyr Trp Phe Ala

```
            115                 120                 125
Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 29
<211> LENGTH: 233
<212> TYPE: PRT
<213> ORGANISM: Artificial sequence
<220> FEATURE:
<223> OTHER INFORMATION: Humanized antibody sequence (h16C3-Abb* light
      chain)
<220> FEATURE:
<221> NAME/KEY: MISC_FEATURE
<222> LOCATION: (1)..(19)
```

<223> OTHER INFORMATION: Leader sequence
<220> FEATURE:
<221> NAME/KEY: MISC_FEATURE
<222> LOCATION: (20)..(127)
<223> OTHER INFORMATION: Variable region
<220> FEATURE:
<221> NAME/KEY: MISC_FEATURE
<222> LOCATION: (128)..(233)
<223> OTHER INFORMATION: Constant region
<220> FEATURE:
<221> NAME/KEY: MISC_FEATURE
<222> LOCATION: (43)..(53)
<223> OTHER INFORMATION: CDR1
<220> FEATURE:
<221> NAME/KEY: MISC_FEATURE
<222> LOCATION: (69)..(75)
<223> OTHER INFORMATION: CDR2
<220> FEATURE:
<221> NAME/KEY: MISC_FEATURE
<222> LOCATION: (108)..(116)
<223> OTHER INFORMATION: CDR3

<400> SEQUENCE: 29

Met Gly Val Pro Thr Gln Leu Leu Leu Trp Leu Thr Val Val Val
1               5                   10                  15

Val Arg Cys Asp Ile Gln Met Thr Gln Ser Pro Ser Ser Leu Ser Ala
            20                  25                  30

Ser Val Gly Asp Arg Val Thr Ile Thr Cys Gln Ala Ser Glu Asn Ile
        35                  40                  45

Tyr Gly Ala Leu Asn Trp Tyr Gln Arg Lys Pro Gly Lys Ser Pro Lys
    50                  55                  60

Leu Leu Ile Tyr Gly Ala Ser Asn Leu Ala Thr Gly Met Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Gln Val Leu Ser
            100                 105                 110

Ser Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 30
<211> LENGTH: 17
<212> TYPE: PRT
<213> ORGANISM: Homo sapiens

<400> SEQUENCE: 30

Leu Ile Ser Thr Tyr Ser Gly Asp Thr Lys Tyr Ser Gln Lys Phe Gln
1               5                   10                  15

Gly

```
<210> SEQ ID NO 31
<211> LENGTH: 17
<212> TYPE: PRT
<213> ORGANISM: Artificial sequence
<220> FEATURE:
<223> OTHER INFORMATION: Humanized antibody sequence

<400> SEQUENCE: 31
```

Leu Ile Ser Thr Tyr Ser Gly Asp Thr Lys Tyr Asn Gln Lys Phe Gln
1               5                   10                  15

Gly

```
<210> SEQ ID NO 32
<211> LENGTH: 10
<212> TYPE: PRT
<213> ORGANISM: Artificial sequence
<220> FEATURE:
<223> OTHER INFORMATION: Humanized antibody sequence (h16C3-Abb* heavy
      chain CDR1)

<400> SEQUENCE: 32
```

Gly Tyr Thr Phe Thr Asp Tyr Ala Met His
1               5                   10

```
<210> SEQ ID NO 33
<211> LENGTH: 16
<212> TYPE: PRT
<213> ORGANISM: Artificial sequence
<220> FEATURE:
<223> OTHER INFORMATION: Humanized antibody sequence (h16C3-Abb* heavy
      chain CDR2)

<400> SEQUENCE: 33
```

Ile Ser Thr Tyr Ser Gly Asp Thr Lys Tyr Asn Gln Asn Phe Gln Gly
1               5                   10                  15

```
<210> SEQ ID NO 34
<211> LENGTH: 12
<212> TYPE: PRT
<213> ORGANISM: Artificial sequence
<220> FEATURE:
<223> OTHER INFORMATION: Humanized antibody sequence (h16C3-Abb* heavy
      chain CDR3)

<400> SEQUENCE: 34
```

Gly Asp Tyr Ser Gly Ser Arg Tyr Trp Phe Ala Tyr
1               5                   10

```
<210> SEQ ID NO 35
<211> LENGTH: 11
<212> TYPE: PRT
<213> ORGANISM: Artificial sequence
<220> FEATURE:
<223> OTHER INFORMATION: Humanized antibody sequence (h16C3-Abb* light
      chain CDR1)

<400> SEQUENCE: 35
```

Gln Ala Ser Glu Asn Ile Tyr Gly Ala Leu Asn
1               5                   10

```
<210> SEQ ID NO 36
<211> LENGTH: 7
<212> TYPE: PRT
<213> ORGANISM: Artificial sequence
```

-continued

```
<220> FEATURE:
<223> OTHER INFORMATION: Humanized antibody sequence (h16C3-Abb* light
      chain CDR2)

<400> SEQUENCE: 36

Gly Ala Ser Asn Leu Ala Thr
1               5

<210> SEQ ID NO 37
<211> LENGTH: 9
<212> TYPE: PRT
<213> ORGANISM: Artificial sequence
<220> FEATURE:
<223> OTHER INFORMATION: Humanized antibody sequence (h16C3-Abb* light
      chain CDR3)

<400> SEQUENCE: 37

Gln Gln Val Leu Ser Ser Pro Tyr Thr
1               5

<210> SEQ ID NO 38
<211> LENGTH: 121
<212> TYPE: PRT
<213> ORGANISM: Artificial sequence
<220> FEATURE:
<223> OTHER INFORMATION: Humanized antibody sequence (h16C3-Abb* heavy
      chain variable)
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (51)..(66)
<223> OTHER INFORMATION: CDR2
<220> FEATURE:
<221> NAME/KEY: MISC_FEATURE
<222> LOCATION: (99)..(110)
<223> OTHER INFORMATION: CDR3

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Met
        35                  40                  45

Gly Leu Ile Ser Thr Tyr Ser Gly Asp Thr Lys Tyr Asn Gln Asn Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 39
<211> LENGTH: 108
<212> TYPE: PRT
<213> ORGANISM: Artificial sequence
<220> FEATURE:
<223> OTHER INFORMATION: Humanized antibody sequence (h16C3-Abb* light
      chain)
<220> FEATURE:
```

```
<221> NAME/KEY: MISC_FEATURE
<222> LOCATION: (24)..(34)
<223> OTHER INFORMATION: CDR1
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (89)..(97)
<223> OTHER INFORMATION: CDR3

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Val Leu Ser Ser Pro Tyr
                85                  90                  95

Thr Phe Gly Gly Gly Thr Lys Leu Glu Ile Lys Arg
            100                 105
```

MONOCLONAL ANTIBODY NEO-201 FOR THE TREATMENT OF HUMAN CARCINOMAS

RELATED APPLICATION DISCLOSURE

This application is a 371 National Stage of International Appl. No. PCT/US2018/059039 International Filing Date Nov. 2, 2018, which claims the benefit of U.S. Provisional Application Ser. No. 62/592,778, filed Nov. 30, 2017, and U.S. Provisional Application Ser. No. 62/581,380, filed Nov. 3, 2017, each of which is hereby incorporated by reference in its entirety.

SEQUENCE LISTING INFORMATION

This application includes as part of its disclosure a biological sequence listing in the file named "1143282o004402.txt", created on May 4, 2020, having a size of 32,601 bytes, which is hereby incorporated by reference in its entirety.

BACKGROUND

Cancer represents one of the most frequent causes of mortality worldwide, with an estimated twenty million new cases expected annually as early as 2025 (Ferlay et al., 2015). Conventional methods of treating cancer such as surgery, radiation, and chemotherapy often elicit severe side-effects yet fail to cure the majority of patients with advanced disease, leading to relapse (Bodey et al., 1996). More recent treatment modalities have been developed to selectively target cancerous cells while largely sparing normal healthy tissues. Among them, immunotherapy has become an important treatment option for cancer patients as it revolutionizes the field of cancer medicine.

An underlying principle of cancer immunotherapy is known as immunoediting (Mittal et al., 2014), which is an extrinsic mechanism of cancer suppression that initiates only after cellular transformation has occurred and intrinsic mechanisms of cancer suppression have failed. The immunoediting process occurs in three phases; elimination, equilibrium, and escape. During the elimination and equilibrium phases, respectively, immune rejection of cancer cells either predominates or balances with cancer cell proliferation to control malignant growth. In the escape phase, however, cancer cells once held in check may escape immune recognition due to insensitivity to immune effector mechanisms and/or induction of immune suppression in the tumor microenvironment. Cancer cells that escape immune recognition are then able to more freely proliferate and grow into clinically apparent disease (Dunn et al., 2004). The aim of cancer immunotherapy is to keep cancer cells in the elimination and/or equilibrium phase by generating and/or amplifying antitumor immune responses to counteract tumor growth, delay tumor recurrence, and prolong survival (Carter, 2001; Hodge et al., 2006; Vergati et al., 2010; Gabitzsch et al., 2015). Therapeutic approaches include treating patients with checkpoint inhibitory antibodies, antitumor vaccines, and chimeric antigen receptor (CAR)-T cells, all of which leverage adaptive immunity by T cells. However, innate immunity can also generate and potentiate antitumor responses, and tumor-targeting monoclonal antibodies (mAbs) can be used to stimulate innate antitumor immunity (Topalian et al., 2011).

NEO-201 is a novel humanized IgG1 mAb that was generated against the Hollinshead allogeneic colorectal cancer vaccine platform (Hollinshead et al., 1970; Hollinshead et al., 1972). The immunogenic components of this vaccine were tumor-associated antigens (TAAs) that were derived from tumor membrane fractions pooled from surgically resected specimens from 79 patients with colon cancer (Hollinshead et al., 1985). These membrane fractions were semi-purified, screened for delayed-type hypersensitivity (DTH) in colon cancer patients versus healthy volunteers, and evaluated in clinical trials in patients with refractory colorectal cancer (Hollinshead et al., 1985; Hollinshead, U.S. Pat. No. 4,810,781, 1989; Bristol & Kantor, U.S. Pat. No. 7,829,678, 2010). These trials reported clinical benefit as defined by both antitumor response and significant prolongation in overall survival in patients that developed a sustained IgG response in addition to a cell-mediated response against the vaccine, thereby suggesting that the vaccine contained immunogenic components capable of generating antitumor antibodies (Hollinshead, 1991). This original colorectal cancer vaccine was used to generate monoclonal antibodies in mice, yielding the previously described ensituximab (NPC-1C/NEO-102) (Luka et al., 2011; Patel et al., 2013; Beg et al., 2016; Kim et al, 2017) and NEO-201. Preliminary investigation indicates that NEO-201 may bind tumor-associated variants of CEACAM family members (Zeligs et al., 2017), and efforts are underway to further characterize the antigen(s) and specific epitope(s) recognized by NEO-201.

The human carcinoembryonic antigen (CEA) family is a composed of 29 genes tandemly arranged on chromosome 19q13.2. Based on nucleotide homologies, these genes are classified into two major subfamilies, the CEACAM and pregnancy-specific glycoprotein subgroups. The CEACAM-encoded proteins include CEA (CEACAM5), CEA-related cell adhesion molecules (CEACAM1, CEACAM3, CEACAM4, CEACAM6, CEACAM7 and CEACAM8. CEACAM family belongs to the Ig superfamily. Structurally, each of the human CEACAMs contain one N-terminal domain that includes 108-110 amino acid and is homologous to Ig variable domains, followed by a different number (zero to six) of Ig C2-type constant-like domains. The CEACAM proteins can interact homophilically and heterophilically with each other. CEACAM1 is a unique protein within this family because it contains an ITIM (immunoreceptor tyrosine-based inhibitory motif) like PD1 in its cytoplasmic domain. This inhibitory effect is triggered by phosphorylation of tyrosine residues with the ITIM, which results in recruitment of the Src homology 2 domain-containing tyrosine phosphatase-1 and −2. The CEACAM1 protein is expressed on a variety of immune cells including monocytes, granulocytes, activated T cells, B cells and NK cells. CEACAM1 occurs as several isoforms, the two major ones being CEACAM1-L and CEACAM1-S that have long (L), or short (S) cytoplasmic domains, respectively. CEACAM1-S expression is totally lacking in human leukocytes. CEACAM1-L is expressed on subpopulation of activated human NK cells that are negative for CD16 but positive for CD56.

Monoclonal antibodies (mAbs) consist of a unique antigen-binding region (fragment antigen-binding, Fab) that is specific to a given mAb, and a constant region (fragment crystallizable, Fc) that is common to all mAbs of the same isotype. The Fc region is capable of modulating immune cell activity by engaging with Fc receptor (FcR) family members expressed on the surface of specific immune cell types. In particular, human IgG1 mAbs can interact with Fc gamma receptor IIIa (FcγRIIIa, CD16) expressed on macrophages and NK cells. This interaction can stimulate macrophages to phagocytose mAb-opsonized cancer cells, and can activate NK cells to degranulate and lyse cancer cells through a mechanism known as antibody-dependent cellular cytotoxicity (ADCC). ADCC has been shown to be a key mediator of antitumor effects in vivo in many preclinical studies, and plays an important role in the mechanism-of-action of several mAbs used for cancer therapy (Seidel et al., 2013). Examples of clinically-approved mAbs that can mediate ADCC include trastuzumab, which targets the HER2 receptor for breast cancer (Seidel et al., 2013; Petriçevic et al., 2013); rituximab, which targets the pan-B-cell marker CD20 for lymphoma (Seidel et al., 2013; Dall'Ozzo et al., 2004); cetuximab, which targets the epidermal growth factor receptor (EGFR) for colorectal and head and neck cancer (Seidel et al., 2013; Levy et al., 2009; Kawaguchi et al., 2007; Lopez-Albaitero et al., 2009); and avelumab, which targets the immunosuppressive ligand PD-L1 for Merckel cell carcinoma and bladder cancer (Boyerinas et al., 2015). Additionally, the Fc region can potentially interact with the C1 complex to activate complement-dependent cellular cytotoxicity (CDC), in which a proteolytic cascade culminates in the formation of pores in the plasma membrane that cause the lysis of cells targeted by the antibody. Even in instances when anti-tumor CDC has been demonstrated in vitro, there is controversy whether it is crucial for the clinical efficacy of mAb therapy in cancer (Meyer et al., 2014).

Applicant's prior U.S. Pat. Nos. 5,688,657, 7,314,622, 7,491,801, 7,763,720, 7,829,678, 8,470,326, 8,524,456, 8,535,667, 8,802,090, 9,034,588, 9,068,014, 9,371,375, 9,592,290, 9,718,866, and RE39,760, each of which is hereby incorporated by reference in its entirety, disclose various anti-cancer antibodies, cancer antigens, and related technologies.

BRIEF DESCRIPTION

Studies described in the examples herein assess in vitro binding characteristics and in vivo activity and localization of NEO-201 in preclinical models. NEO-201 exhibited broad reactivity against a range of human carcinoma cell lines and tumor tissues, but was not observed to bind the majority of healthy tissues. In addition, NEO-201 exhibited both ADCC and CDC activity against human carcinoma cells in vitro, and largely attenuated the growth of human pancreatic xenograft tumors in vivo both alone and in combination with human peripheral blood mononuclear cells (PBMCs) as the effector cell source for ADCC. Finally, a single-dose toxicity study in non-human primates demonstrated safety and tolerability of NEO-201, as a transient decrease in circulating neutrophils was the only adverse effect observed. These studies provide the rationale for the potential clinical utility of NEO-201 as a novel therapeutic agent for the treatment of a wide variety of solid tumors. Additionally, the observed CDC activity of the subject antibodies opens the opportunity to treat immunocompromised patients in which ADCC is not expected to be effective, as for example in patients that are immunocompromised because of their disease or as an effect of radiation, chemotherapy, and other disease treatments.

We have previously reported the preclinical antitumor activity (Patel et al., 2013) as well as clinical safety and efficacy (Beg et al., 2016; Kim et al, 2017) for a mAb generated against the Hollinshead allogeneic colorectal cancer vaccine platform, termed ensituximab (NPC-1C/NEO-102). This report describes the characterization of the second tumor antigen-targeting mAb derived from the same vaccine platform, called NEO-201. NEO-201 is shown to positively stain a variety of human carcinoma cell lines in vitro, including cells derived from a variety of tumor types, histological subtypes, and mutational profiles. NEO-201 positivity was more frequently observed in tumor cell lines derived from lung adenocarcinomas versus squamous cell carcinomas, and in HER2 positive breast cancer cell lines versus triple negative lines. The staining of human tumor samples demonstrated that a wide variety of carcinoma tissues stained positively for NEO-201, including the colon, pancreatic, stomach, lung, breast, and uterine tumors. An expanded investigation with larger sample sizes may reveal that NEO-201 can discriminate between histological and/or molecular subtypes among various carcinomas. Intriguingly, a higher proportion of tumor tissues reacted with NEO-201 in contrast to cultured cancer cell lines. This observation may indicate that the target recognized by NEO-201 is expressed more readily in vivo than in vitro, which would suggest that target expression is at least partially dependent upon tumor cell interaction with factors from within the local microenvironment. Experiments are currently in progress to further characterize the antigen(s) and epitope(s) recognized by NEO-201, and to determine the regulatory control mechanism(s) which govern its expression in tumor tissue but not normal tissue.

This investigation also revealed that NEO-201 is remarkably tumor-specific in its staining profile, as the overwhelming majority of healthy normal tissues and normal tissues adjacent to tumor tissue were found to be negative for NEO-201. Although NEO-201 positivity was observed in normal tongue and exocervix tissues, the staining intensity was weak and the microarray represented only a minimal sample size (n=2). Further expanded analysis of NEO-201 staining in normal tissue samples will be undertaken to confirm these observations. Furthermore, NEO-201 administration did not induce any grossly observable toxicity in mice, and was well-tolerated when administered to nonhuman primates. The observed depletion of neutrophils in nonhuman primates suggests that the antigen(s) reactive with NEO-201 are expressed on these immune cells, and assessment of NEO-201 reactivity with hematopoietic cell types is ongoing. These encouraging results suggest that 1) NEO-201 may have diagnostic utility in discriminating cancerous from benign tissue from patient biopsies; and 2) NEO-201 may effectively target tumors without provoking significant toxicity or off-target effects other than neutropenia. Efforts are currently underway to further evaluate the safety and tolerability of NEO-201, and a clinical trial using NEO-201 for the treatment of carcinoma is being planned.

Innate immune effector mechanisms have been shown to play a major role in promoting and potentiating host anti-tumor immunity. The Fc portion of human IgG1 mAbs is well-known to activate innate immunity against opsonized targets, potentially mediating ADCC and/or CDC (Strome et al., 2007; Hayes J, et al., 2017). In particular, the ability to mediate ADCC is regarded as a key component of therapeutic efficacy for various human IgG1 mAbs approved for the treatment of cancer (Boyerinas et al., 2015; Seidel et al., 2013; Petricevic et al., 2013 Dall'Ozzo et al., 2004; Levy et al., 2009; Kawaguchi et al., 2007; Lopez-Albaitero et al., 2009). Importantly, a V158F polymorphism in the FCGR3A gene (encoding FcγRIIIa) is associated with differential affinity for human IgG1 mAbs (Koene et al., 1997; Wu et al., 1997), with immune cells from donors with the high affinity V/V genotype exhibiting greater trastuzumab-mediated ADCC activity in vitro (Musolino et al., 2008). The V/V genotype was also shown to significantly correlate with objective response rate and progression-free survival in breast cancer patients treated with trastuzumab (Musolino et al., 2008), thereby providing indirect clinical evidence for role of ADCC in mAb-based therapy. NEO-201 can mediate ADCC in vitro, as treatment of tumor cells with NEO-201 enhanced the cytotoxic activity of NK cells by 2-5-fold, and ADCC activity was retained at even low concentrations of antibody (0.1 µg/mL). These data raise the possibility that patients with the V/V genotype may derive added benefit from NEO-201 treatment. An additional prospect is the potential to enhance ADCC activity, and presumably the potential clinical benefit of NEO-201, by augmenting NK cell function with cytokine stimulation. IL-2 is well-known to be a potent activator of NK cells (Hank et al., 1990), and IL-21 was shown to enhance ADCC activity mediated by trastuzumab and cetuximab (Watanabe et al., 2010). Recent preclinical studies with a novel fusion protein superagonist of IL-15 signaling, termed ALT-803, have demonstrated greatly enhanced proliferation, activation, and lytic capability of NK cells (and CD8+ T cells), leading to significant antitumor activity in various animal models of cancer (Han et al., 2011; Gomes-Giacoia et al., 2014; Mathios et al., 2016; Rhode et al., 2016; Kim et al., 2016; Felices et al., 2017). Intriguingly, ALT-803 was found to substantially enhance in vitro NK cell degranulation, IFN-γ production, and rituximab-mediated ADCC against B cell lymphoma cell lines and primary follicular lymphoma cells, and combination treatment with ALT-803 and rituximab in two B cell lymphoma models in vivo resulted in significantly reduced tumor cell burden and improved survival (Rosario et al., 2016).

Another innate immune effector mechanism potentially engaged by mAbs is activation of the complement system to promote CDC, and NEO-201 was found to possess the ability to mediate CDC to kill tumor cells. The contribution of CDC to the therapeutic efficacy of mAbs is controversial but has been suggested to be beneficial for cancer therapy, at least in some specific instances (Meyer et al., 2014). Additionally, several different complement-regulatory proteins (CRPs) function to inhibit complement activation, and certain membrane-bound CRPs such as CD46, CD55, and CD59 were reported to be aberrantly expressed in various cancers (Seya et al., 1994; Niehans et al., 1996; Donin et al., 2003) which likely confers resistance to CDC. Future investigations will ascertain whether strategies to block CRPs can enhance NEO-201-mediated CDC of resistant tumor cells.

Evaluation of NEO-201 in vivo revealed profound antitumor effects when dosed in combination with activated human immune effector cells. This combination even led to full regressions in some of the mice (5/20, 25%) from the two combination groups. Moreover, NEO-201 was found to preferentially localize to the xenograft tumor tissue but not to various healthy tissues. These data confirm that a mechanism-of-action for NEO-201 against tumors is the ADCC-dependent lysis of tumor cells by innate immune cells. However, it should be noted that antitumor activity was also observed with NEO-201 alone without the addition of human immune cells to the immunodeficient mice. This phenomenon may be specific to conditions encountered in vivo, as treatment of CFPAC-1 tumor cells with NEO-201 did not induce substantial toxicity in the ADCC assays in vitro. One hypothesis for NEO-201 activity in the absence of immune effector cells may be the induction of CDC. CDC activity of NEO-201 was directly demonstrated in further experiments described in Example 3.

In summary, this investigation has demonstrated that NEO-201 is a remarkably tumor-specific antibody that is capable of engaging innate immune effector mechanisms including both ADCC and CDC to kill tumor cells. In addition, NEO-201 demonstrated safety and antitumor efficacy in an in vivo xenograft model of pancreatic cancer, as well as tolerability in nonhuman primates. These findings provide the supporting rationale for the clinical development of NEO-201 as a diagnostic and therapeutic agent for patients with a broad variety of carcinomas. The results also support use of NEO-201 in immunocompromised patients (having low NK cell levels), because the anti-tumor effects can result from CDC even in the absence of robust ADCC activity.

BRIEF DESCRIPTION OF THE SEVERAL VIEWS OF THE DRAWINGS

FIGS. 1A-1D: Flow cytometry of NEO-201 binding to human carcinoma cell lines. Representative human carcinoma cell lines with various levels of NEO-201 antigen expression, (FIG. 1A) pancreatic CFPAC-1 (high), (FIG. 1B) NSCLC H441 (medium), (FIG. 1C) breast HCC1937 (low), and (FIG. 1D) colon SW1116 (negative). Results are expressed as % NEO-201 positive and mean fluorescence intensity (MFI) for each cell line. Red, NEO-201-stained cells; black, unstained cells. NEO-201 positivity was defined as % positive≥10%.

(FIG. 2A) Representative NEO-201 staining from adjacent normal and malignant tissues from colon, pancreas, stomach, and lung samples. All images were obtained at 100×. (FIG. 2B) Quantification of NEO-201 positive staining from the human tumor microarray samples from various carcinoma tissues. (FIG. 2C) Quantification of NEO-201 positive staining from human tumor microarray samples from normal tissue adjacent to tumor tissue. n=number of samples.

FIGS. 3A-3C: NEO-201 mediates ADCC and CDC against human tumor cell lines. (FIG. 3A) ADCC activity using CFPAC-1 or ASPC-1 cells as target cells. Cells were treated with 10 µg/mL of NEO-201 or human IgG1 (negative control). Purified NK cells from two healthy donors were used as effector cells at the indicated E:T ratios. *, statistically significant (p<0.05) by T-test. (FIG. 3B) ADCC assay using CFPAC-1 cells treated with increasing doses of NEO-201. NK cells isolated from a healthy donor were used as effector cells at an E:T ratio of 12.5:1. The graph depicts the fold increase in % specific lysis of NEO-201-treated tumor cells versus that of control cells treated with 10 µg/mL human IgG1. *, statistically significant (p<0.05) by T-test. (FIG. 3C) CDC assay using ASPC-1 cells treated with the indicated doses of NEO-201 for the indicated durations. *statistically significant (p<0.05) by T-test.

(FIG. 4A) Tumor volume measurements for the CFPAC-1 xenografts from each treatment group at various time points. Mice (n=10 animals/group) were dosed intraperitoneally with saline solution, human IgG1 (250 µg), or NEO-201 (100 and 250 µg) on days 13, 17, and 20 post tumor cell implantation. Mice were also dosed intraperitoneally with ~1.0×10$^7$ IL-2-activated human PBMCs on days 14, 18, and 21 as a source of immune effector cells. (FIG. 4B) Quantification of the number of mice still bearing palpable tumors on day 36. (FIG. 4C) Representative image of NEO-201-treated versus saline-treated tumor-bearing mice. (FIG. 4D) Body weight measurements of the tumor-bearing mice at various time points during the study.

(FIG. 6A) Percent change in body weight relative to baseline (day −1) measured for monkeys at 7 days and 14 days after a receiving a single dose of NEO-201 at the indicated dose levels. n=4 animals per group (2 females, 2 males). (FIG. 6B) Percent change in neutrophil levels relative to baseline (day −7) from the blood of monkeys treated with a single dose of NEO-201 at the indicated dose levels. n=4 animals per group (2 females, 2 males). (FIG. 6C) p values for neutrophil levels versus 0 mg/kg controls for each dosage and time point. *statistically significant (p<0.05) by T-test.

(FIG. 6A-6B) Percentage specific lysis of H520 lung carcinoma (FIG. 6A) or OV90 ovarian carcinoma (FIG. 6B) cells treated with NEO-201 (upper line, square symbols) or IgG1 negative control (lower line, round symbols) at 4 hours as a function of Effector:Target (E:T) ratio. E:T ratios were 6.25:1, 12.5:1, or 25:1. mAb concentration was 10 μg/mL. Values shown are mean+/−SD of 3 replicates. Asterisk (*) indicates statistical significance vs. IgG negative control (p<0.01, 2-tailed t-test). (FIG. 6C) Percentage specific lysis of lung (H520, HCC827), breast (ZR-75-1), and ovarian (OV90) carcinomas cells treated with NEO-201 (right, lightly grey bars) or negative control IgG (left, solid black bars) at four hours at a constant E:T ratio of 25:1. mAb concentration was 10 μg/mL. Values shown are mean+/−SD of 3 replicates. Asterisk (*) indicates statistical significance vs. IgG negative control (p<0.01, 2-tailed t-test).

FIG. 8: Treatment with ALT-803 enhance ADCC activity mediated by NEO-201. NK cells isolated from two normal donors were treated with ALT-803 (25 ng/ml) or medium control for 48 hours and used as effector cells in a 4 h non radioactive ADCC assay using Celigo Imaging cytometer. CF-PAC1 (human pancreatic cancer cell line) cells were stained with calcein AM and used as targets at 3,000 cells/well. Results are expressed in % specific lysis (SE).

FIG. 9: Treatment with ALT-803 enhanced the expression of TIM-3 and NKG2D on human NK cells. Purified human NK cells from a normal donor were cultured for 48 hours with or without ALT-803 (25 ng/ml). Results are expressed in % of positive cells (MFI).

FIG. 10: Treatment with ALT-803 enhanced the expression of TIM-3 and NKG2D on human NK cells. Purified human NK cells from another normal donor were cultured for 48 hours with or without ALT-803 (25 ng/ml). Results are expressed in % of positive cells (MFI).

FIG. 11: Treatment with ALT-803 enhance ADCC activity mediated by low concentrations NEO-201. NK cells isolated from a normal donor (ND#6) were treated with ALT-803 (25 ng/ml) or medium control for 48 hours and used as effector cells in a 4 h non radioactive ADCC assay using Celigo Imaging cytometer. NEO-201 was used at three different concentrations (10 μg/ml, 1 μg/ml, and 0.1 μg/ml). CF-PAC1 (human pancreatic cancer cell line) cells were stained with calcein AM and used as targets at 3,000 cells/well. E:T=25:1. Results are expressed in % specific lysis (SE). * Statistically significant (p<0.01).

FIG. 12: Treatment with ALT-803 enhances ADCC activity of a normal donor (ND#8) with minimal ADCC activity mediated by and NEO-201 and the activity can be blocked by anti-CD16 and anti-TIM-3 antibody. NK cells isolated from a normal donor with minimal ADCC activity and were treated with ALT-803 (25 ng/ml) or medium control for 48 hours and used as effector cells in a 4 h non radioactive ADCC assay using Celigo Imaging cytometer. Anti-CD16 and anti-TIM-3 were used at a concentrations of 30 μg/ml and 15 μg/ml. NK cells were pretreated with anti-CD16 or anti-TIM-3 for 2 hour prior to the addition of NEO-201 and effector cells. CF-PAC1 (human pancreatic cancer cell line) cells were stained with calcein AM and used as targets at 3,000 cells/well. NEO-201 was used at a concentration of 10 μg/ml. E:T=25:1. Results are expressed in % specific lysis (SE). *Statistically significant (p<0.01) compared to no ALT-803 treatment. #Statistically significant (p<0.01) compared to no anti-CD16 and anti-TIM-3 treatment.

FIG. 13: NK-92 killing assay using NEO-201 (16 hr). Target tumor cells (ASPC-1, BxPC-3, CFPAC-1, or LS174T) were seeded at 3000 cells/well. The cells were then treated with 10 μg/mL of either human IgG1 isotype control antibody or NEO-201, and then the natural killer (NK) cell line NK-92 was added at effector-to-target (E:T) ratios of 1.5625:1, 3.125:1, 6.25:1, and 12.5:1. After 16 hr incubation at 37° C., cell viability was quantified using the Celigo Imaging Cytometer and GraphPad Prism 7 software. Live target cells (calcein AM+/PI−) were counted for each well, and specific lysis was calculated. Results are shown graphically and tabulated below for each tumor cell type. *statistically significant (p<0.05).

DETAILED DESCRIPTION

Figure 2B:
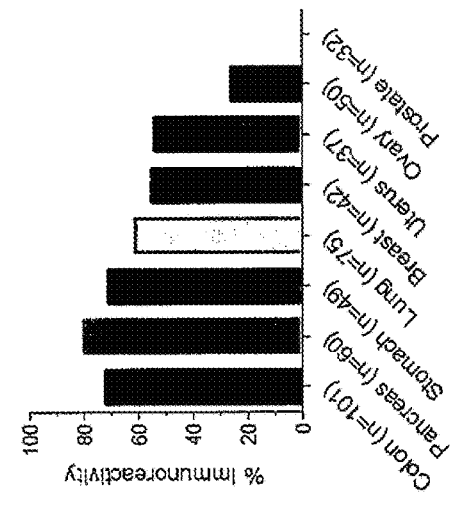
FIGS. 2A-2C: IHC staining of human tumor samples by NEO-201.

In one aspect, the disclosure provides a method of killing carcinoma cells comprising administering an effective amount of a NEO-201 antibody to a patient in need thereof.

In one aspect, the disclosure provides a method of treating a carcinoma, comprising administering an effective amount of a NEO-201 antibody to a patient in need thereof.

In one aspect, the disclosure provides a method of preventing the recurrence of a carcinoma, comprising administering an effective amount of a NEO-201 antibody to a patient in need thereof.

In one aspect, the disclosure provides a method of decreasing the tumor burden in a patient having a carcinoma, comprising administering an effective amount of a NEO-201 antibody to a patient in need thereof.

Said antibody may mediate complement mediated cytotoxicity (CDC), thereby killing carcinoma cells in said patient.

Said patient may be natural killer ("NK")-depleted prior to or at the time of said administering. Said patient may be severely NK-depleted prior to or at the time of said administering. Said patient may have NK cell deficiency (NKD), such as CNKD (e.g., CNKD1, CNKD2), or FNKD (e.g., FNKD1). Said patient may be NK-depleted or severely NK-depleted as a result of another therapy, e.g., a cancer therapy, such as chemotherapy or radiotherapy. Said patient may been treated with one or more proteasome inhibitors (e.g., Bortezomib, MG132), Histone deacetylase, inhibitors (e.g., valproic acid, Trichostatin A, Suberoylanilide-hydroxamic acid (SAH), Sodium butyrate), genotoxic agents (e.g., doxorubicin, melphalan, cisplatin, Ara-C, aphidicolin, mitomycin, methotrexate, etoposide), GSK inhibitors (e.g., LiCl, BIO, SB21), BET inhibitors (e.g., JQ1), HSP90 inhibitors (e.g., radicicola), 17-AAG), microtubule assembly inhibitors (e.g., vincristine, cytochalasin D, nocodazole, docetaxel), and/or immunomodulatory drugs (e.g., lenalidomide).

The method may include, prior to or at the time of said administering, determining whether said patient is NK-depleted.

The method may include, prior to or at the time of said administering, determining whether said patient is severely NK-depleted.

In said method, prior to or at the time of said administering, NK cells may comprise less than 5% of the peripheral blood mononuclear cells (PBMCs) in said individual.

In said method, prior to or at the time of said administering, NK cells may comprise less than 3% of the peripheral blood mononuclear cells (PBMCs) in said individual.

In said method, prior to or at the time of said administering, less than 70% of PBMC NK cells in said patient may be CD56dimCD16+ NK cells.

In said method, prior to or at the time of said administering, less than 50% of PBMC NK cells in said patient may be CD56dimCD16+ NK cells.

Said NEO-201 antibody may comprise at least one, two, three, four, five, or all six of the CDR sequences contained in SEQ ID NO: 28 and SEQ ID NO: 29.

Said NEO-201 antibody may comprise a variable heavy chain sequence having at least 90% identity to SEQ ID NO: 38.

Said NEO-201 antibody may comprise a variable light chain sequence having at least 90% identity to SEQ ID NO: 39.

Said NEO-201 antibody may comprise a variable heavy chain sequence having at least 90% identity to SEQ ID NO: 38 and a variable light chain sequence having at least 90% identity to SEQ ID NO: 39.

Said NEO-201 antibody may comprise a heavy chain sequence having at least 90% identity to amino acids 20-470 of SEQ ID NO: 28 and a light chain sequence having at least 90% identity to amino acids 20-233 of SEQ ID NO: 29.

Said NEO-201 antibody may comprise all six of the CDR sequences contained in SEQ ID NO: 28 and SEQ ID NO: 29.

Said NEO-201 antibody may comprise a human IgG1 constant domain.

Said NEO-201 antibody may be humanized.

Said NEO-201 antibody may be conjugated to another moiety.

Said NEO-201 antibody may be conjugated to another cytotoxic moiety, label, radioactive moiety, or affinity tag.

Said method may further comprise administering to the patient an effective amount of a cytokine agonist to potentiate or stimulate killing of cells of said carcinoma. Said cytokine agonist may comprise interleukin-2 (IL-2), interleukin 21 (IL-21), ALT-803, IL-15 inhibitors, checkpoint inhibitors, anti-PD1, anti-PDL1, anti-CTLA-4, anti-41BB, anti-OX40, anti-Tim-3, or a combination thereof.

Said method may further comprise administering to said patient an effective amount of a complement-regulatory protein (CRP) antagonist to potentiate or stimulate killing of cells of said carcinoma. Said CRP antagonist may antagonize one or more of CD46, CD55, or CD59. Said CRP antagonist may comprise an antibody or antigen-binding fragment thereof.

Said cytokine agonist may comprise an IL-15 agonist or an IL-15 superagonist.

Said cytokine agonist may comprise a complex consisting of an IL-15 mutant (IL-15N72D) bound to an IL-15 receptor α/IgG1 Pc fusion protein, such as ALT-803.

The effective dosage of said NEO-201 antibody may be reduced compared to treatment with the NEO-201 antibody alone without said cytokine agonist.

Said carcinoma may comprise colon cancer. Said carcinoma may comprise pancreatic cancer. Said carcinoma may comprise ovarian cancer. Said carcinoma may comprise stomach cancer. Said carcinoma may comprise lung cancer. Said carcinoma may comprise breast cancer. Said carcinoma may comprise uterine cancer.

In another embodiment, the disclosure provides a method of killing carcinoma cells comprising administering an effective amount of a NEO-201 antibody to a patient in need thereof, wherein said patient is natural killer ("NK")-depleted prior to or at the time of said administering. Said NK-depletion may comprise the patient having less than 5% or less than 3% of the peripheral blood mononuclear cells (PBMCs) being NK cells in a sample derived from the patient, e.g., in a blood sample. Alternatively or in addition, prior to or at the time of said administering, less than 70% (or optionally less than 50%) of PBMC NK cells in said patient may be CD56dimCD16+ NK cells.

In another embodiment, the disclosure provides a method of treating a carcinoma, comprising administering an effective amount of a NEO-201 antibody to a patient in need thereof, wherein said patient is natural killer ("NK")-depleted prior to or at the time of said administering.

In another embodiment, the disclosure provides a method of preventing the recurrence of a carcinoma, comprising administering an effective amount of a NEO-201 antibody to a patient in need thereof; wherein said patient is natural killer ("NK")-depleted prior to or at the time of said administering.

In another embodiment, the disclosure provides a method of decreasing the tumor burden in a patient having a carcinoma, comprising administering an effective amount of a NEO-201 antibody to a patient in need thereof, wherein said patient is natural killer ("NK")-depleted prior to or at the time of said administering.

In the foregoing methods, said antibody may mediate CDC, thereby, thereby killing carcinoma cells in said patient, e.g., notwithstanding the absence of effective ADCC due to the patient being NK-depleted. Said patient may be severely NK-depleted at the time of said administering. Optionally, the method further comprises determining whether said patient is NK-depleted or severely NK-deleted, e.g., at the time of said administering or within a period prior to said administering, such as within 1 or 2 weeks prior. NK-depleted or severely NK-depleted status may also be inferred from the patient's history, such as the prior or concurrent use of another therapy that depletes NK cells. For example said patient have undergone or be concurrently undergoing cancer therapy, such as radiotherapy or chemotherapy. Said cancer therapy may include administration of one or more one or more proteasome inhibitors (e.g., Bortezomib, MG132), Histone deacetylase inhibitors (e.g., valproic acid, Trichostatin A, Suberoylanilide-hydroxamic acid (SAH), Sodium butyrate), genotoxic agents (e.g., doxorubicin, melphalan, cisplatin, Ara-C, aphidicolin, mitomycin, methotrexate, etoposide), GSK inhibitors (e.g., LiCl, BIO, SB21), BET inhibitors (e.g., JQ1), HSP90 inhibitors (e.g., radicicola), 17-AAG), microtubule assembly inhibitors (e.g., vincristine, cytochalasin D, nocodazole, docetaxel), and/or immunomodulatory drugs (e.g., lenalidomide).

Said patient may have NK cell deficiency (NKD), such as CNKD (e.g.,CNKD1, CNKD2), or FNKD (e.g., FNKD1).

In a preferred embodiment of the invention which may be used with any of the foregoing or following embodiments, said NEO-201 antibody may comprise at least one, two, three, four, five, or all six of the CDR sequences contained in SEQ ID NO: 28 and SEQ ID NO: 29.

In a preferred embodiment of the invention which may be used with any of the foregoing or following embodiments, said NEO-201 antibody may comprise a variable heavy chain sequence having at least 80%, at least 85%, at least 90% or most preferably at least 95% identity to SEQ ID NO: 38. Said variable heavy chain having said percentage sequence identity may comprise all 3 of the CDR sequences contained in SEQ ID NO: 38.

In a preferred embodiment of the invention which may be used with any of the foregoing or following embodiments, said NEO-201 antibody may comprise a variable light chain sequence having at least 80%, at least 85%, at least 90% or most preferably at least 95% identity to identity to SEQ ID NO: 39. Said variable light chain may comprise all 3 of the CDR sequences contained in SEQ ID NO: 39.

In a preferred embodiment of the invention which may be used with any of the foregoing or following embodiments, said NEO-201 antibody may comprise a variable heavy chain sequence having at least 80%, at least 85%, at least 90% or most preferably at least 95% identity to SEQ ID NO: 38 and a variable light chain sequence having at least 80%, at least 85%, at least 90% or most preferably at least 95% identity to identity to SEQ ID NO: 39. Said variable light chain may comprise all 3 of the CDR sequences contained in SEQ ID NO: 39, and said variable heavy chain having said percentage sequence identity may comprise all 3 of the CDR sequences contained in SEQ ID NO: 38.

In a preferred embodiment of the invention which may be used with any of the foregoing or following embodiments, said NEO-201 antibody may comprise a heavy chain sequence having at least 80%, at least 85%, at least 90% or most preferably at least 95% identity to amino acids 20-470 of SEQ ID NO: 28 and a light chain sequence having at least 80%, at least 85%, at least 90% or most preferably at least 95% identity to amino acids 20-233 of SEQ ID NO: 29. Said light chain may comprise all 3 of the CDR sequences contained in SEQ ID NO: 29, and said heavy chain having said percentage sequence identity may comprise all 3 of the CDR sequences contained in SEQ ID NO: 28.

In a preferred embodiment of the invention which may be used with any of the foregoing or following embodiments, said NEO-201 antibody may comprise the heavy chain variable region sequence contained in SEQ ID NO: 28 and the light chain variable region sequence contained in SEQ ID NO: 29.

In a preferred embodiment of the invention which may be used with any of the foregoing or following embodiments, said NEO-201 antibody may comprise a heavy chain sequence containing amino acids 20-470 of SEQ ID NO: 28 and a light chain sequence containing amino acids 20-233 of SEQ ID NO: 29.

In a preferred embodiment of the invention which may be used with any of the foregoing or following embodiments, said NEO-201 antibody comprises a human IgG1 constant domain.

In a preferred embodiment of the invention which may be used with any of the foregoing or following embodiments, said NEO-201 antibody may be humanized.

In a preferred embodiment of the invention which may be used with any of the foregoing or following embodiments, said NEO-201 antibody may be conjugated to another moiety, such as another cytotoxic moiety, label, radioactive moiety, or affinity tag.

In a preferred embodiment of the invention which may be used with any of the foregoing or following embodiments, said method may further comprise administering to the patient an effective amount of a cytokine agonist to potentiate or stimulate killing of cells of said carcinoma. Said cytokine agonist may comprise interleukin-2 (IL-2), interleukin 21 (IL-21), ALT-803, IL-15 inhibitors, checkpoint inhibitors, anti-PD1, anti-PDL1, anti-CTLA-4, anti-41BB, anti-OX40, anti-Tim-3, or a combination thereof.

In a preferred embodiment of the invention which may be used with any of the foregoing or following embodiments, said method may further comprise administering to said patient an effective amount of a complement-regulatory protein (CRP) antagonist to potentiate or stimulate killing of cells of said carcinoma. Said CRP antagonist may antagonize one or more of CD46, CD55, or CD59. Said CRP antagonist may comprise an antibody or antigen-binding fragment thereof. Said cytokine agonist may comprise an IL-15 agonist or an IL-15 superagonist. Said cytokine agonist may comprises complex consisting of an IL-15 mutant (IL-15N72D) bound to an IL-15 receptor α/IgG1 Fc fusion protein. Said cytokine agonist may comprise ALT-803.

In a preferred embodiment of the invention which may be used with any of the foregoing or following embodiments, the effective dosage of said NEO-201 antibody is reduced compared to treatment with the NEO-201 antibody alone without said cytokine agonist.

In a preferred embodiment of the invention which may be used with any of the foregoing or following embodiments, said cancer may express the NEO-201 antigen. Said expression of NEO-201 antigen may be determined by detecting the NEO-201 antigen in a sample of said cancer. Said detecting may be performed by techniques including but not limited to histological staining, flow cytometry, RT-PCR, dot blotting, Western blotting, Northern Blotting, and other techniques known in the art. In the case of a recurrent or metastatic cancer, expression of NEO-201 antigen may also be inferred by the expression of NEO-201 in the primary cancer, or by responsiveness of the primary cancer to NEO-201 antibody therapy.

In a preferred embodiment of the invention which may be used with any of the foregoing or following embodiments, said cancer may comprise colon cancer.

In a preferred embodiment of the invention which may be used with any of the foregoing or following embodiments, said cancer may comprise pancreatic cancer.

In a preferred embodiment of the invention which may be used with any of the foregoing or following embodiments, said cancer may comprise ovarian cancer.

In a preferred embodiment of the invention which may be used with any of the foregoing or following embodiments, said cancer may comprise stomach cancer.

In a preferred embodiment of the invention which may be used with any of the foregoing or following embodiments, said cancer may comprise lung cancer.

In a preferred embodiment of the invention which may be used with any of the foregoing or following embodiments, said cancer may comprise breast cancer.

In a preferred embodiment of the invention which may be used with any of the foregoing or following embodiments, said cancer may comprise uterine cancer.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "NK-depleted" or "natural killer-depleted" as used herein refer to a patient having low natural killer (NK) cell levels relative to the normal range. NK cells are a cytotoxic innate immune lymphocyte. Typically, NK cells comprise 5-20% of the peripheral blood mononuclear cells (PBMCs) in a healthy individual. A patient having NK cells comprising less than 5% of the PMBCs is referred to as NK-depleted. Additionally, a patient is referred to as severely NK-cell depleted if NK cells comprising less than 3% of the PMBCs. Additionally, in normal individuals, up to 90% of PBMC NK cells are $CD56^{dim}CD16^+$ NK cells, and these are considered the most cytotoxic subset. If less than 70% of PBMC NK cells are $CD56^{dim}CD16^+$ NK cells, then the patient is referred to as NK-depleted. Additionally, if less than 50% of PBMC NK cells are $CD56^{dim}CD16^+$ NK cells, then the patient is referred to as severely NK-depleted. A given patient may be referred to as NK-depleted or severely NK-depleted based on meeting either or both of these individual criteria. Generally speaking, a patient's status as NK-depleted or severely NK-depleted is determined by testing a sample taken from the patient, e.g., a blood sample, e.g., a sample obtained and tested within one or two weeks prior. A patient's status as NK-depleted or severely NK-depleted may also be inferred from a disease diagnosis and/or a course of treatment that is associated with such depletion of NK cells.

NK-depleted also includes subjects having an NK cell deficiency (NKD). Exemplary NKD conditions include Classical NKD (CNKD), characterized by an absence of NK cells and their function among peripheral blood lymphocytes; Functional NKD (FNKD), characterized by presence of NK cells within peripheral blood lymphocytes, having defective NK cell activity. In both CNKD and FNKD the NK cell abnormality is a major immunological deficit, which results in inadequate ADCC responses. CNKD and FNKD can be further subdivided based on patient characteristics such as the identity of causative gene(s) and other patient characteristics. CNKD includes CNKD subtype 1 (CNKD1), which is autosomal dominant and is associated with defects in the GATA2 gene, and CNKD subtype 2 (CNKD2), which is autosomal recessive and is associated with defects in the MCM4 gene. FNKD includes FNKD1, which is autosomal recessive and is associated with defects in the FCCR3A gene.

"Antibody," as used herein, refers broadly to any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, from all sources, e.g., human, rodent, rabbit, cow, sheep, pig, dog, chicken, are considered to be "antibodies." Antibodies include but are not limited to chimeric antibodies, human antibodies and other non-human mammalian antibodies, humanized antibodies, single chain antibodies (scFvs), camelbodies, nanobodies, IgNAR (single-chain antibodies derived from sharks), small-modular immunopharmaceuticals (SMIPs), and antibody fragments (e.g., Fabs, Fab', F(ab')$_2$.) Numerous antibody coding sequences have been described; and others may be raised by methods well-known in the art. See Streltsov, et al. (2005) *Protein Sci.* 14(11): 2901-9; Greenberg, et al. (1995) *Nature* 374(6518): 168-173; Nuttall, et al. (2001) *Mol Immunol.* 38(4): 313-26; Hamers-Casterman, et al. (1993) *Nature* 363(6428): 446-8; Gill, et al. (2006) *Curr Opin Biotechnol.* 17(6): 653-8.

"NEO-201 antibody" refers to an antibody containing the heavy and light chains of SEQ ID NOs: 28 and 29 or the variable regions optionally together with the constant regions contained therein, as well as fragments and variants thereof. Such variants include sequences containing one, two, three, four, five or preferably all six of the CDR sequences contained in SEQ ID NO: 28 and SEQ ID NO: 29, i.e., the heavy chain CDR1 of SEQ ID NO: 32, the heavy chain CDR2 of SEQ ID NO: 33, the heavy chain CDR3 of SEQ ID NO: 34, the light chain CDR1 of SEQ ID NO: 35, the light chain CDR2 of SEQ ID NO: 36, and the light chain CDR3 of SEQ ID NO: 37. Said antibody may be humanized. Said antibody may be expressed containing one or more leader sequences, which may be removed during expression and/or processing and secretion of the antibody. Said antibody may be presented in a monovalent, bivalent, or higher multivalent format, including without limitation a bispecific or multispecific antibody containing said NEO-201 antibody sequence and a binding fragment of a different antibody. Typically said antibody specifically binds to carcinoma cells and competes for binding to carcinoma cells with an antibody comprising the variable heavy chain of SEQ ID NO: 38 and variable light chain of SEQ ID NO: 39, or comprising the heavy chain of SEQ ID NO: 28 and light chain of SEQ ID NO: 29. One or more of those CDR sequences contained in SEQ ID NO: 28 and/or SEQ ID NO: 29 may be substituted with a variant sequence, such as the light chain CDR1 of SEQ ID NO: 1 or 4; light chain CDR2 of SEQ ID NO: 2 or 5; light chain CDR3 of SEQ ID NO: 3 or 6; heavy chain CDR1 of SEQ ID NO: 7; heavy chain CDR2 of SEQ ID NO: 8,10, 30, or 31; heavy chain CDR3 of SEQ ID NO: 9 or 11; or SEQ ID NOs: 30-31. The light chain may comprise the CDRs contained in the light chain sequence of SEQ ID NO: 14, 16, 17, 18, 19, 20, 21, or 29. The heavy chain may comprise the CDRs contained in the heavy chain sequence of SEQ ID NO: 15, 22, 23, 24, 25, 26, 27, or 29. Said antibody may comprise a variable heavy chain sequence having at least 75%, 80%, 85%, 90%, 95%, 96%, 97%, 98%, or 99% identity to SEQ ID NO: 38, and/or a variable light chain sequence having at least 75%, 80%, 85%, 90%, 95%, 96%, 97%, 98%, or 99% identity to SEQ ID NO: 39, optionally wherein said heavy and/or light chain sequence contains one, two, three, four, five or preferably all six of the CDR sequences contained in SEQ ID NO: 28 and SEQ ID NO: 29, i.e., the heavy chain CDR1 of SEQ ID NO: 32, the heavy chain CDR2 of SEQ ID NO: 33, the heavy chain CDR3 of SEQ ID NO: 34, the light chain CDR1 of SEQ ID NO: 35, the light chain CDR2 of SEQ ID NO: 36, and the light chain CDR3 of SEQ ID NO: 37. Said antibody may be conjugated to another moiety, such as a cytotoxic moiety, radioactive moiety, label, or purification tag.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. Antigens may be tumor specific (e.g., expressed by neoplastic cells of pancreatic and colon carcinoma.)

"Cancer," as used herein, refers broadly to any neoplastic disease (whether invasive or metastatic) characterized by abnormal and uncontrolled cell division causing malignant growth or tumor.

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug; or the variable region, or a portion thereof, is altered, replaced or exchanged with a variable region having a different or altered antigen specificity.

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "Sequences of Proteins of Immunological Interest" National Institutes of Health, Bethesda, Md. These expressions include the hypervariable regions as defined by Kabat, et al. (1983) "Sequences of Proteins of Immunological Interest" U.S. Dept. of Health and Human Services or the hypervariable loops in 3-dimensional structures of antibodies. Chothia and Lesk (1987) *J Mol. Biol.* 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) *Methods* 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Differentially present," as used herein, refers broadly to differences in the quantity or quality of a marker present in a sample taken from patients having a disease or condition as compared to a comparable sample taken from patients who do not have one of the diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker may be considered to be differentially present. Optionally, a relatively low amount of up-regulation may serve as the marker.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Framework region" or "FR," as used herein, refers broadly to one or more of the framework regions within the variable regions of the light and heavy chains of an antibody. See Kabat, et al. (1987) "*Sequences of Proteins of Immunological Interest*," National Institutes of Health, Bethesda, Md. These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"High affinity," as used herein, refers broadly to an antibody having a KD of at least $10^{-8}$ M, more preferably at least $10^{-9}$ M and even more preferably at least $10^{-10}$ M for a target antigen. However, "high affinity" binding can vary for other antibody isotypes. For example, "high affinity" binding for an IgM isotype refers to an antibody having a KD of at least $10^{-7}$ M, more preferably at least $10^{-8}$ M.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to a cell that contains an expression vector and supports the replication or expression of the expression vector. Host cells may be prokaryotic cells such as *E. coli*, or eukaryotic cells such as yeast, insect (e.g., SF9), amphibian, or mammalian cells such as CHO, HeLa, HEK-293, e.g., cultured cells, explants, and cells in vivo.

"Hybridization," as used herein, refers broadly to the physical interaction of complementary (including partially complementary) polynucleotide strands by the formation of hydrogen bonds between complementary nucleotides when the strands are arranged antiparallel to each other.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Isolated," as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody").

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) *Short Protocols in Molecular Biology* ($5^{th}$ Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5 M sodium phosphate, 7% SDS at 65° C., followed by one or more washes at 0.2×SSC, 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington, D.C.

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. *Antigens* (*Chapter* 3) Immunology (5$^{th}$ Ed.) New York: W. H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient".

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (1987) *CSH Symp. Quant. Biol.* LII: 123-33; Frier, et al. (1986) *PNAS* 83: 9373-77; Turner, et al. (1987) *J. Am. Chem. Soc.* 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Subjects" as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans. Any mammalian subject in need of being treated according to the present invention is suitable. Human subjects of both genders and at any stage of development (i.e., neonate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., tumor growth, metastasis). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., tumor growth, metastasis). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., tumor growth, metastasis).

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a plasmid, cosmid, phagemid, phage DNA, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector.

The techniques and procedures are generally performed according to conventional methods well known in the art and as described in various general and more specific references that are cited and discussed throughout the present specification. See, e.g., Sambrook, et al. (2001) *Molec. Cloning: Lab. Manual* [$3^{rd}$ Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

EXAMPLES

The invention now being generally described, it will be more readily understood by reference to the following examples, which are included merely for purposes of illustration of certain aspects and embodiments of the present invention, and are not intended to limit the invention.

Example 1

NEO-201 Binds to Various Human Carcinoma Cell Lines

Flow cytometry analysis was used to profile a panel of human carcinoma cell lines for NEO-201 binding. The staining profile is summarized in Table 1, and representative histograms from cell lines with high, medium, low, and negative staining is shown in FIGS. 1A-C. Assessment of the binding activity of NEO-201 revealed that 3/6 (50%) colon cancer cell lines and 4/5 (80%) pancreatic cancer cell lines were highly positive. When non-small cell lung carcinoma (NSCLC) cell lines of various histological subtypes were profiled, it was determined that 3/5 (60%) of adenocarcinoma cell lines reacted with NEO-201, while only 1/4 (25%) of squamous cell carcinoma cell lines were found to be positive. Screening of breast cancer cell lines was also conducted. Of the cell lines that expressed either the estrogen receptor (ER) or the progesterone receptor (PR), whether alone or in combination with HER2, 2/4 (50%) stained positively for NEO-201. Of the HER2+ cell lines, whether alone or in combination with ER or PR, 3/4 (75%) were recognized by NEO-201. However, NEO-201 staining was found at low levels on only 1/4 (25%) of triple-negative breast cancer cell lines. In total, 15/30 (50%) of tested tumor cell lines were recognized by NEO-201. These data indicate that NEO-201 is reactive against a broad range of in vitro cultured tumor cell lines, and show that distinct differences in antibody reactivity can occur based upon tumor subtype.

Example 2

NEO-201 Tissue Staining is Highly Tumor-Specific

Figure 2C:
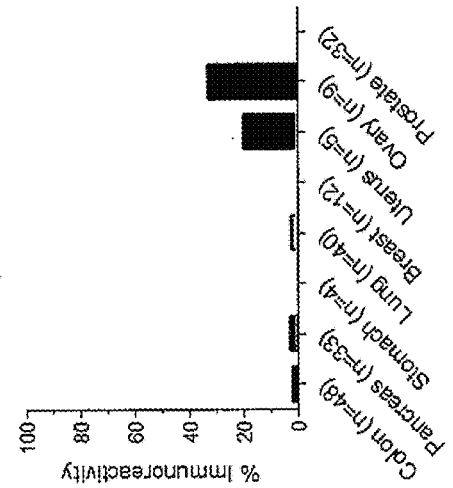
Figure 2A:
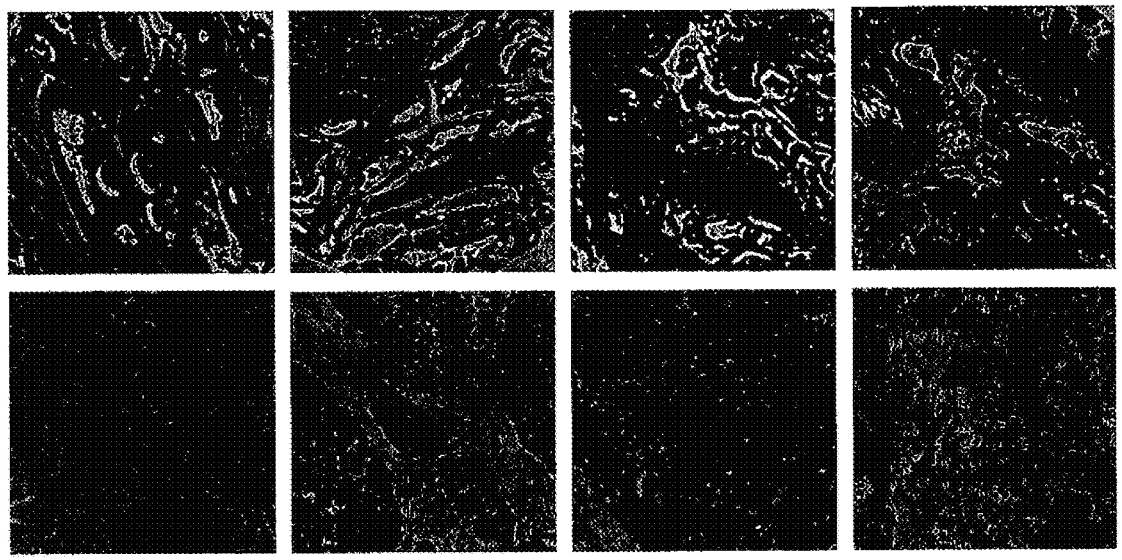

Immunohistochemistry was used to investigate NEO-201 reactivity from human tumor samples using tissue microarrays representing dozens of samples for each cancer type. As shown in FIG. 2A, immunoreactivity U.S. Pat. No. 7,829,678 with NEO-201 was completely absent from normal colon, pancreas, and lung tissues, but was highly positive in the tumor tissues from these organs. Strikingly, staining was found only on the tumor cells, as the surrounding stromal cells were not stained (FIG. 2A). IHC staining and of the microarray samples determined that NEO-201 was highly reactive against colon cancer (72%), pancreatic cancer (80%), stomach cancer (71%), lung cancer (61%), breast cancer (55%), and uterine cancer (54%). Additionally, a sizeable minority of ovarian cancer (26%) samples also exhibited positive staining, but no staining was observed in prostate cancer tissues (FIG. 2B). Overall, 258/345 (74.7%) of sampled tumor tissues stained positively for NEO-201. Importantly, NEO-201 reactivity was almost entirely absent from normal healthy tissues (Table 2) and from the normal tumor-adjacent tissues with the exception of some uterine and ovarian sample (FIG. 2C). However, the number of tissues in this set of uterine and ovarian tissues was limited (5 and 9 samples, respectively). Altogether, these data indicate that NEO-201 recognizes tumor tissues from a wide variety of carcinomas and is highly tumor-specific.

Example 3

NEO-201 Mediates ADCC and CDC to Kill Tumor Cells

As a humanized IgG1 antibody, NEO-201 is theorized to be capable of mediating ADCC to kill tumor cells that express the NEO-201 antigen. To investigate this potential mechanism of action, ADCC assays utilizing human natural killer (NK) cells isolated from PBMCs from two different healthy donors were performed on cell lines highly positive for NEO-201 staining (CFPAC-1 and ASPC-1). Treatment with NEO-201 was observed to enhance the killing of both CFPAC-1 and ASPC-1 cells to levels 2 to 6-fold greater than the killing of control IgG1-treated tumor cells (FIG. 3A). Titration assays were also conducted, and revealed that NEO-201 retains the ability to significantly induce ADCC at doses as low as 0.1 µg/mL (FIG. 3B).

CDC is a complex cascade of proteolytic cleavages that culminates in the activation of the membrane attack complex that lyses antibody-bound target cells. Certain human IgG1 antibodies are capable of mediating CDC, however, CDC is dependent on the antigen specificity of the antibody. CDC assays revealed that NEO-201 induces complement-mediated lysis of ASPC-1 cells in a manner that was dependent upon both mAb dose and incubation time (FIG. 3C). Altogether, these data demonstrate that NEO-201 effectively engages innate immune effector mechanisms to specifically lyse antibody-bound tumor cells in vitro.

Example 4

Figure 4B:
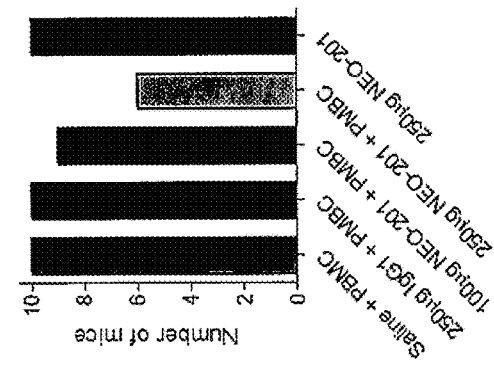
FIGS. 4A-4D: Antitumor efficacy of NEO-201 in CFPAC-1 tumor xenografts.
Figure 4D:
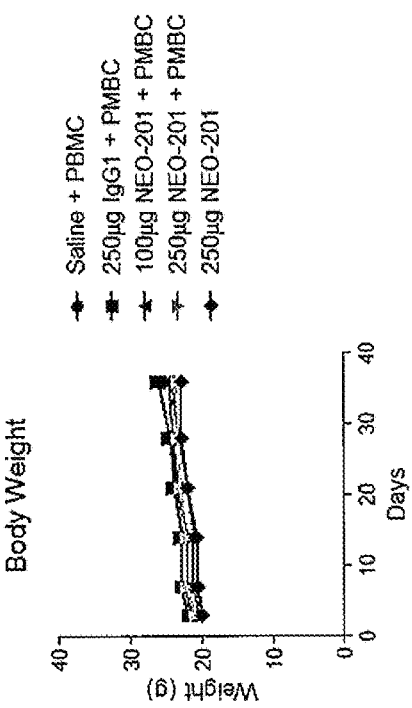
Figure 4A:
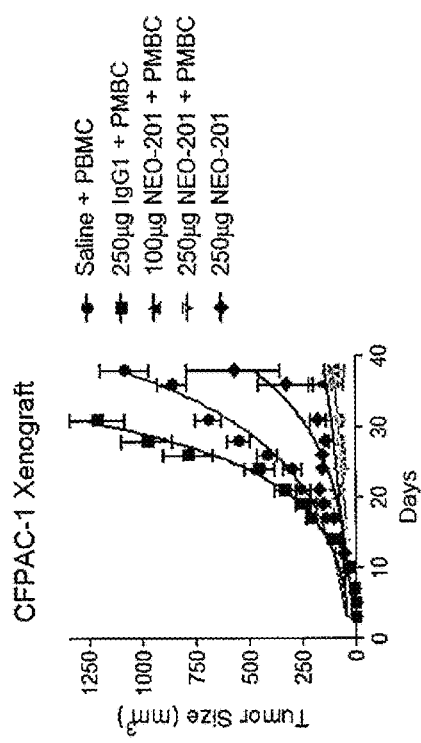
Figure 4C:

NEO-201 Reduces the Growth of Tumor Xenografts Alone and in Combination with Human PNMC Effector Cells To determine the potential antitumor efficacy of NEO-201, CFPAC-1 cells were grown as tumor xenografts in immunocompromised NU/NU nude mice. These cells were chosen based upon their high expression level of NEO-201 antigen and high sensitivity to NEO-201-mediated ADCC. Once the CFPAC-1 tumors had grown to approximately 100 $mm^3$ in size, tumor-bearing mice were injected three times with saline, 250 mg human IgG1, 100 µg NEO-201, or 250 µg NEO-201 followed by three injections of $1.0 \times 10^7$ IL-2-activated (200 U/mL) human PBMCs to function as ADCC-mediating effector cells. As shown in FIG. 4A, NEO-201+ PBMCs induced a substantial reduction in tumor growth at both dose levels compared to either the saline+PBMCs or human IgG+PBMCs control groups. Whereas no mice from the control groups were tumor-free on day 36, 1 of 10 (10%) and 4 of 10 (40%) mice had no palpable tumor remaining from the NEO-201 100 µg+PBMCs and the NEO-201 250 µg+PBMCs groups, respectively (FIG. 4B). In addition, another group of mice were dosed with NEO-201 without the addition of human PBMCs, and a significant reduction in tumor growth relative to the control groups was observed (FIGS. 4A, C). Importantly, monitoring of the body weights of the tumor-bearing mice revealed no weight reduction in any of the treatment groups (FIG. 4D). Collectively, these results indicate that NEO-201 is capable of substantially reducing tumor growth though both ADCC and non-ADCC mechanisms (such as CDC) without inducing significant toxicity in mice.

Example 5

NEO-201 Localizes at the Xenograft Tumor Site

Figure 5A:
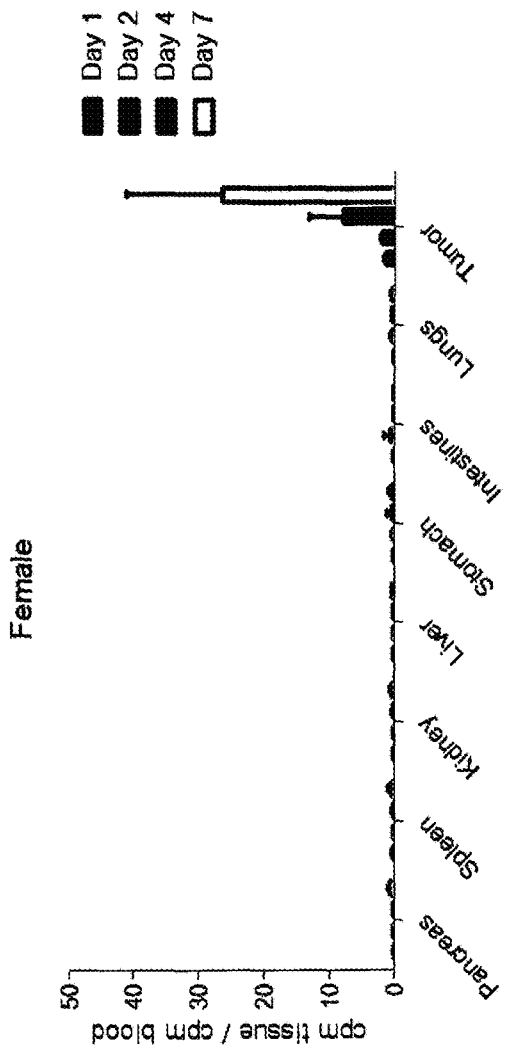
FIGS. 5A-5B: NEO-201 biodistribution in CFPAC-1 xenograft-bearing mice. Measurement of normalized radioactivity from the indicated tissues of CFPAC-1 tumor-bearing female (FIG. 5A) and male (FIG. 5B) mice dosed intravenously with radiolabeled NEO-201. n=4 animals/time point. Day 1, 2, 4, and 7 represents the amount of time between radiolabeled antibody injection and necropsy.
Figure 5B:
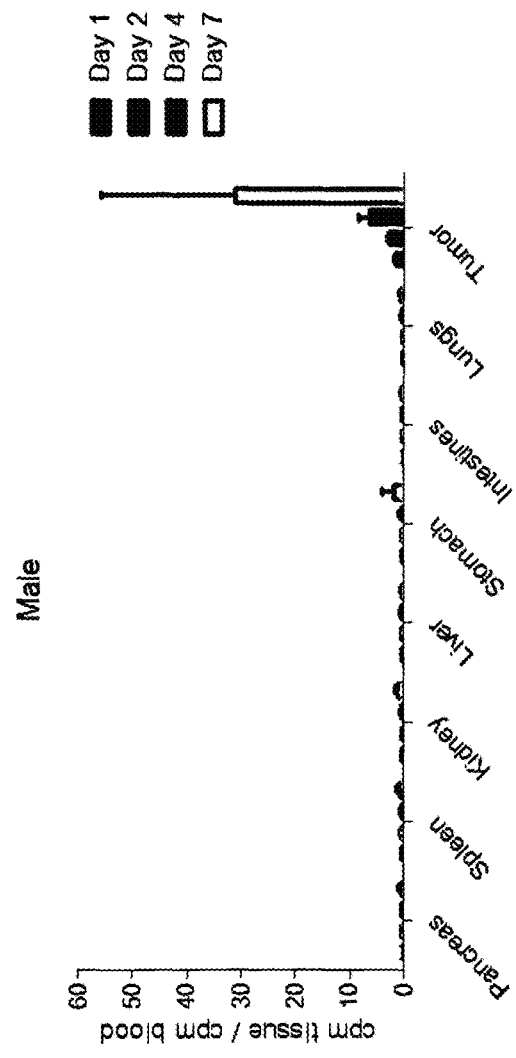

Biodistribution studies were conducted utilizing radiolabeled NEO-201 in female and male NU/NU nude mice with established CFPAC-1 xenograft tumors. These mice were injected intravenously with the radiolabeled antibody, and then blood, organs, and tumors were harvested for analysis at various time points post-injection. Low levels of radioactivity were found in the pancreas, spleen, kidney, liver, stomach, intestines, and lungs in both male and female mice at all time points (FIGS. 5A, B). However, normalized uptake of radioactivity was substantially higher in tumors versus all other tissues at all time points, with tumor radioactivity progressively rising to levels 20-30 times higher than those of the blood by day 7 (FIGS. 5A, B). Quantitatively similar results were obtained for both female and male mice. These results indicate that NEO-201 preferentially localizes to malignant tissue that expresses the target antigen, and does not accumulate in normal tissues.

Example 6

NEO-201 Pharmacokinetics and Toxicity Evaluation in Non-human Primates

A single-dose study was conducted in purpose-bred cynomolgus monkeys to determine NEO-201 pharmacokinetics and associated toxicity. Cynomolgus monkeys were selected because this species is closely related to humans both phylogenetically and physiologically, and is a species commonly used for nonclinical toxicity evaluations. Male and female animals received a single intravenous infusion of NEO-201 diluted in saline at dose levels of 5 mg/kg, 20 mg/kg, and 49 mg/kg, which was the highest achievable dose per infusion volume. Blood samples were drawn in all animals pre-injection and at various time points post-injection up to 14 days, and serum preparations were assessed for NEO-201 levels by ELISA. As depicted in Table 3, quantifiable and dose-dependent serum concentrations of NEO-201 were observed through the last collection time point (14 days post-dose). As expected for an intravenous administration, Tmax values peaked by 10 min for the majority of the animals from all groups (10/12, 83%), with the exception of one male and one female animal each from the 5 mg/kg group. Over the dose range evaluated, peak (Cmax) exposure was dose proportional; total (AUC) exposure was greater than dose proportional at the lowest doses and approximately proportional from 20 mg/kg to 49 mg/kg. Differences in exposure at the lowest dose were attributed to an approximately 2-fold greater mean clearance (CL) and lesser volume of distribution (Vz). Mean half-life (HL) was 167 (20 mg/kg) or 170 (49 mg/kg) hours at the higher doses, approximately 3.7-fold greater than at the 5 mg/kg dose (46.2 hr). Sex-differences were not observed.

Figures 6A, 6B:
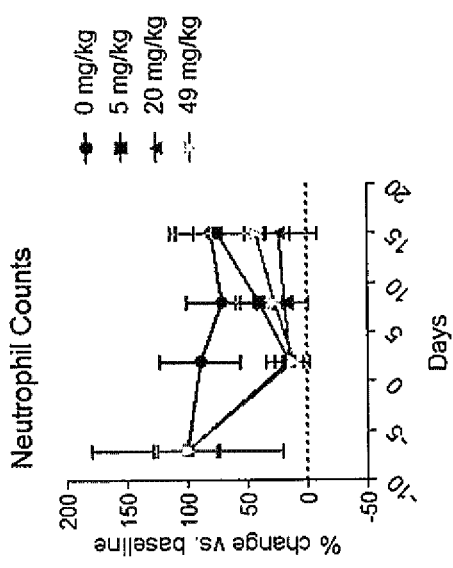
FIGS. 6A-6C: Body weight and neutrophil counts from cynomolgus monkeys treated with NEO-201.
Figure 6C:
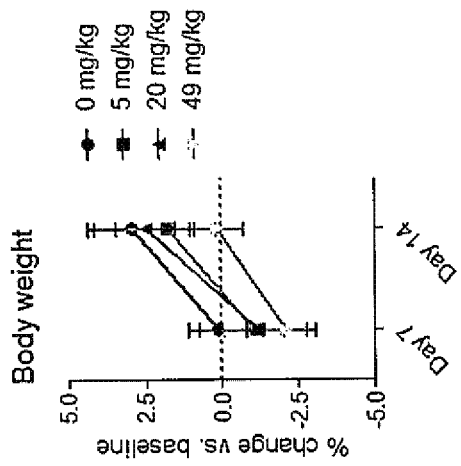
Figure 7A:
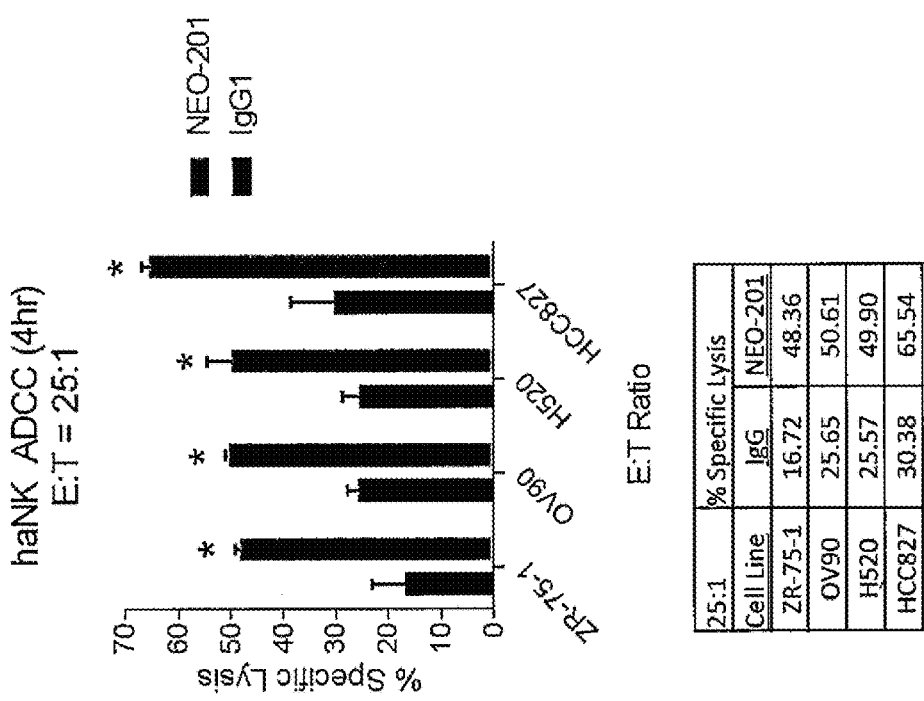
FIGS. 7A-7C: haNK ADCC assay using NEO-201 (4 hr). Target cells=3000 cells/well.
Figure 7B:
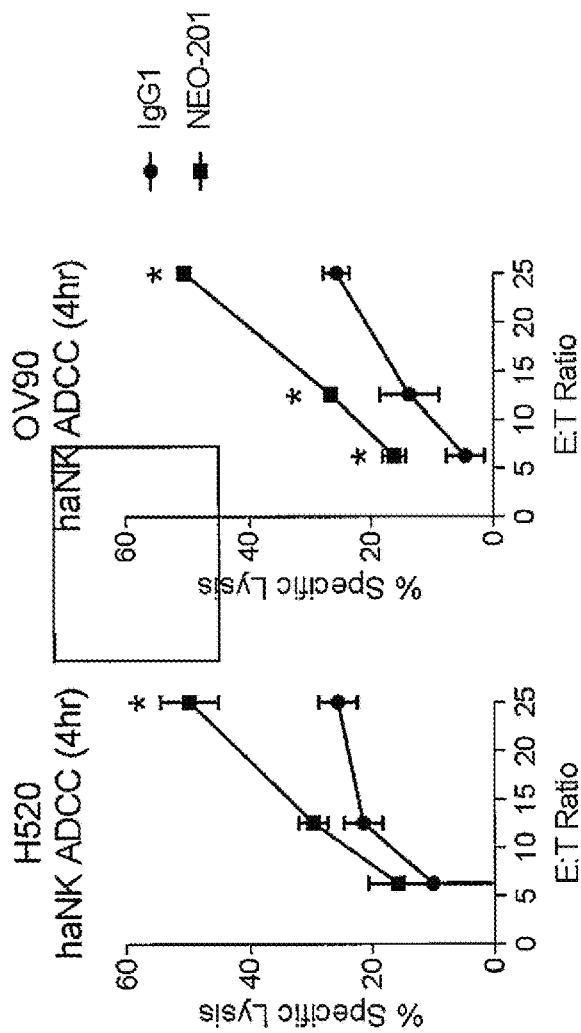
Figure 7C:
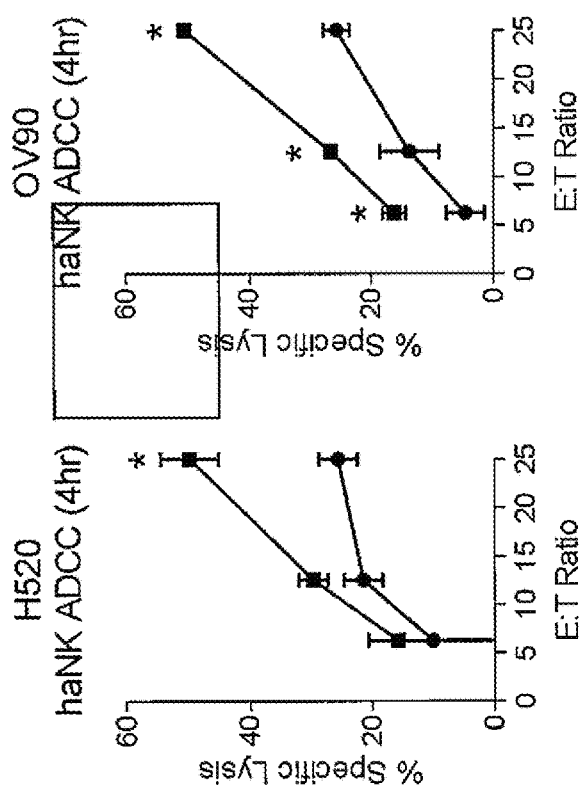

Observations and examinations to determine toxicity over the course of the 14 day study included 1) periodic clinical evaluations; 2) measurement of food consumption and body weight; and 3) urine and blood evaluations, including urinalysis, hematology, coagulation tests, serum chemistry, and toxicokinetics. As shown in FIG. 6A, none of the dose level groups experienced a change in body weight>3% from their pre-injection weight, and no individual monkeys experienced a change>7%. Food consumption remained unchanged for all but two animals in the 5 mg/kg dose group who had low consumption on day 11 only. There were no significant changes from baseline (before NEO-201 injection) through day 15 in any of the serum chemistry, urinalysis, or coagulation tests (see Materials and Methods for details). The main laboratory change in blood counts was a decrease in neutrophil counts relative to baseline (FIG. 6B). The decreases were of varying magnitudes, ranging from mild to marked, and a clear dose-response was not evident. For the majority of animals this was a transient finding, as improvements were typically noted by day 8 (FIG. 6B). By day 15, neutrophil counts were observed to recover nearly totally or partially for the 5 mg/kg group or the 20 mg/kg and 49 mg/kg groups, respectively (FIG. 6B). The recovery of neutrophil counts by day 15 is reflected in the statistical comparison to the 0 mg/kg animals, which were significantly different at day 2 for all 3 dosage levels (p<0.05) but not significantly different at days 8 and 15 for two out of three dosage groups (p>0.05) (FIG. 6C).

Example 7

Materials and Methods
Cell Lines and Culture

The following human carcinoma cell lines were obtained from the American Type Culture Collection (Manassas, Va.): colon (COLO 205, HT-29, LS174T, SW1116, SW1463, SW480, SW620), pancreas (ASPC-1, CFPAC-1, PANC-1), breast (AU-565, BT-474, BT-549, HCC1500, HCC1937, HCC38, MDA-MB-231, MDA-MB-468, SK-BR-3, T-47D, ZR-75-1), and lung (CALU-1, H1703, H226, H441, H520, H522, H596, HCC4006, HCC827, SK-LU-1). All cell cultures were maintained in RPMI 1640, DMEM, or IMDM culture medium (Corning, Corning, N.Y.) as designated by the provider for propagation and maintenance. Culture medium was supplemented with 10% USA-sourced and heat-inactivated HyClone fetal bovine serum defined (GE Healthcare Life Sciences, Issaquah, Wash., USA), 100 U/mL penicillin, 100 µg/mL streptomycin (Corning Life Science, Manassas, Va., USA). PBMCs from healthy volunteer donors were obtained from the National Institutes of Health Clinical Center Blood Bank (NCT00001846) under the appropriate Institutional Review Board approval and informed consent.

Generation of the Humanized NEO-201 Monoclonal Antibody

The Hollinshead colon cancer specific vaccine was used as the immunogenic material to generate monoclonal antibodies in mice. The method for the preparation of tumor-associated proteins and peptides has been previously described (Hollinshead, U.S. Pat. No. 4,810,781, 1989). In brief, cancer tissue was minced and used to generate a single cell suspension that was then subjected to hypotonic saline membrane extraction, a series of centrifugation steps, and followed with low frequency sonication. The resulting membrane-extracted proteins were fractionated on Sephadex G-200 resin or by electrophoretic methods, then concentrated and quantitated (Hollinshead et al, 1970; Hollinshead et al., 1972; Hollinshead et al., 1985). The TAA preparation was admixed with complete Freund's adjuvant and injected subcutaneously in BALB/c mice. This was followed by 3 booster injections in incomplete Freund's adjuvant, separated by 2-3 weeks. Mouse serum was tested by ELISA for antibody responses against the immunizing antigen and mice with potent responses were used to generate immortalized hybridoma cells by fusing the mouse B cells from the spleen with the SP2/0-Ag14 myeloma cell line and selecting cells that grew and produced mouse immunoglobulins (IgGs). From these mouse IgGs, the murine 16C3 clone (m16C3) was chosen based upon reactivity with colon tumor cell membrane extract derived from LS174T or HT-29 cells as determined by ELISA. The cDNAs encoding the heavy and light chain IgG1 were determined from RNA isolated from hybridoma clone 16C3 E12 and shown to be unique (Bristol & Kantor, U.S. Pat. No. 7,829,678, 2010). The m16C3 protein sequence was humanized as h16C3 and designated NEO-201. Humanization was performed in silica by replacing mouse sequences outside the complementarity-determining regions (CDRs) of the Fab region of both heavy and light chain proteins with human Fab sequences, and retaining the three mouse CDR sequences from each chain. The Fc regions of the heavy and light chains were selected from human IgG1 isotype used in other humanized approved mAb products. The amino acid sequence was back-translated to DNA, which was optimized for protein expression in CHO cells. The DNA for heavy and light chain h16C3 was then synthesized chemically, cloned into mammalian expression plasmids, and transfected into mammalian cell lines (HEK293T and CHO). Several stable CHO cell lines expressing recombinant h16C3 were derived and banked. Purified recombinant h16C3 was retested in studies which verified that the humanized 16C3 antibody had similar characteristics as the original m16C3 antibody (Bristol & Kantor, U.S. Pat. No. 7,829,678, 2010).

The NEO-201 antibody sequences used in these examples are contained in the following illustration:

H16C3-Abb*Heavy Chain:
(SEQ ID NO: 28)
MGWSCIIFFLVATATGVHS/QVQLVQSGAEVKKPGASVKVSCKASGYTFT

DYAMHWVRQAPGQRLEWMGLISTYSGDTKYNQNFQGRVTMTVDKSASTAY

MELSSLRSEDTAVYYCARGDYSGSRYWFAYWGQGTLVTVSS/ASTKGPSV

FPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK

H16C3-Abb*Light Chain:
(SEQ ID NO: 29)
MGVPTQLLLLWLTVVVVRC/DIQMTQSPSSLSASVGDRVTITCQASENIY

GALNWYQRKPGKSPKLLIYGASNLATGMPSRFSGSGSGTDYTFTISSLQP

EDIATYYCQQVLSSPYTFGGGTKLEIK/TVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC

The boundaries between the expression leader sequence, variable region, and constant region is delimited by a forward slash ("/") in each sequence, and CDR sequences are shown in bold, underlined text. The antibody sequences used included the variable and constant regions shown. These include the heavy chain CDR1 of SEQ ID NO: 32, the heavy chain CDR2 of SEQ ID NO: 33, the heavy chain CDR3 of SEQ ID NO: 34, the light chain CDR1 of SEQ ID NO: 35, the light chain CDR2 of SEQ ID NO: 36, and the light chain CDR3 of SEQ ID NO: 37.

Flow Cytometry

Binding of NEO-201 to human carcinoma cell lines was analyzed by flow cytometry. Cells ($1.0 \times 10^6$) were incubated with 1 µL per test of LIVE/DEAD Fixable Aqua (Thermo Fisher Scientific, Waltham, Mass., USA) in 1× phosphate buffered saline (PBS) for 30 min at 4° C. to accomplish live versus dead cell discrimination. Cells were then centrifuged, washed twice with cold PBS, and then stained with Pacific Blue-conjugated NEO-201 antibody (BioLegend, San Diego, Calif.) in 1× PBS+1% BSA (Teknova, Hollister, Calif., USA) for 30 minutes at 4° C. After staining, cells were washed twice with cold PBS and examined using a FACSVerse flow cytometer (BD Biosciences, San Jose, Calif., USA). Analysis of cellular fluorescence was performed using BD FACSuite software (BD Biosciences, San Jose, Calif., USA). Staining values>10% positive were considered positive for NEO-201 expression. Positive cell lines were ranked according to their quantified expression level (% positive×MFI), and then sorted into groups of low (<200), medium (200-1000), and high (<1000) expression.

Immunohistochemistry (IHC)

Tissue microarrays for colon samples (C0808, C0951) were obtained from US Biomax (Rockville, Md.), and AccuMax tissue microarrays for colon (A303(I)), pancreas (A207(II), A307), stomach (A209), lung (A206(V), A306), breast (A202(VI), A712), uterus (A212), ovary (A212, A213 (II)), prostate (A302(IV)), and various normal (A103(VII)) samples were obtained from Accurate Chemical and Scientific Corporation (Westbury, N.Y.). NEO-201 was biotinylated using the Biotin Protein Labeling Kit (Roche, Basel, Switzerland) as per manufacturer's instructions. Slides were baked at 60° C. for 20 min, deparaffinized with xylene, and rehydrated with a graded ethanol series. Slides were then subjected to peroxide blocking using Peroxidazed I solution (Biocare Medical, Concord, Calif.) for 2 min, avidin blocking using avidin solution (Biocare Medical, Concord, Calif.) for 10 min, biotin blocking using biotin solution (Biocare Medica, Concord, Calif.) for 10 min, and protein blocking using CAS-Block histochemical reagent (Thermo Fisher Scientific, Waltham, Mass.) for 10 min. Slides were then incubated at room temperature with negative control biotinylated human IgG1 kappa (Ancell, Bayport, Minn.) or biotinylated NEO-201 at 10 µg/mL diluted in 1× PBS for 2 hr. Detection was enabled with Dako streptavidin-HRP conjugate (Agilent Technologies, Santa Clara, Calif.) at 1:300 for 30 min, incubation with DAB peroxidase substrate (Thermo Fisher Scientific, Waltham, Mass.) for 1-3 min, and counterstaining with hematoxylin. Each microarray tissue spot was evaluated by light microscopy for cell staining intensity using the following scale: 0 (negative), ± (equivocal), 1+ (weak), 2+(moderate), 3+ (strong). A tissue spot was recorded as positive if it contained cells stained with intensity≥1.

Antibody-dependent Cellular Cytotoxicity (ADCC) Assay

ADCC assays were performed using a modification of a previously described procedure (Boyerinas et al., 2015). Negative selection of NK cells from normal human donor PBMCs was performed using the EasySep Human NK Cell Isolation Kit (StemCell Technologies, Vancouver, BC, Canada) according to the manufacturer's protocol. Purified NK cells were incubated overnight in RPMI-1640 medium supplemented with L-glutamine, 10% FBS, and antibiotics. On the day of the assay, target cells (CFPAC-1, ASPC-1) were labeled with 10 µM Calcein AM cell-permeant dye (Termo Fisher Scientific, Waltham, Mass., USA) for 30 min and then seeded in triplicate at $3.0 \times 10^3$ cells/well into black-walled flat-bottom 96-well culture plates (#655090 Greiner bio-one, Germany). Tumor cells were then treated with 10 µg/mL of human IgG1 isotype control antibody (Thermo Fisher Scientific, Waltham, Mass., USA) or NEO-201 unless otherwise indicated, and then NK cells were added at effector-to-target (E:T) ratios of 12.5:1 and 25:1. After 4 hr incubation at 37° C., 10 µg/mL the propidium iodide (Thermo Fisher Scientific, Waltham, Mass., USA) was added to each well and the plate was imaged and analyzed using the Celigo Imaging Cytometer (Nexcelom Bioscence LLC, Lawrence, Mass., USA). Live target cells (calcein AM+/PI−) were counted for each well, and specific ADCC lysis was calculated as follows: % specific lysis=100−[(average live target count$_{experimental}$/average live target count$_{control}$)×100].

Complement-dependent Cytotoxicity (CDC) Assay

CDC assays were performed using a modification of a previously described procedure (Konishi et al., 2008). ASPC-1 target cells were labeled with Calcein AM as described above and seeded at $5.0 \times 10^3$ cells/well into black-walled 96-well plates. Cells were then treated with 0.5 or 5.0 µg/mL NEO-201 for 15 min at 37° C. to opsonize the cells, and then purified rabbit complement (MP Biomedicals, Santa Ana, Calif.) was added to each well at a 1:8 dilution. After incubation at 37° C. for 30, 60, or 120 min, propidium iodide was added, plates were imaged and analyzed using the Celigo Imaging Cytometer, and specific lysis was calculated as described above for ADCC activity.

Xenograft Antitumor Assay

Tumors were established in 6-week old female athymic NU/NU nude mice (Charles River Laboratories International, Wilmington, Mass.) by implanting a suspension of cultured tumor cells in 1× PBS subcutaneously in the right flank of the mice. Once tumors reached ~100 mm³ in size, mice were sorted by tumor volume and randomized into 5 groups (n=10 animals). Mice were then injected intraperitoneally with vehicle alone (saline solution), human IgG1 (250 μg), or NEO-201 (100 and 250 μg) on days 13, 17, and 20 post implantation. Mice also received intraperitoneal injection of approximately $1.0 \times 10^7$ human PBMCs activated with IL-2 (200 U/mL treated overnight in culture) on days 14, 18, and 21 as a source of immune effector cells. One group of mice was treated similarly with NEO-201 but did not receive human PBMCs. Tumors were measured with a digital calipers every 2-3 days, and tumor volumes were calculated according to the formula (width²×length)/2=mm³, where width was the shorter of the two measurements. Mice were also weighed weekly as a gross measure of general health. Mice with tumor volumes >2000 mm³ were sacrificed according to IACUC guidelines.

Biodistribution Analysis

The biodistribution study was evaluated in tumor-bearing mice using radiolabeled NEO-201 (by Comparative Biosciences, Sunnyvale, Calif.) using a procedure described previously (Patel et al., 2013). Briefly, male and female athymic NU/NU nude mice (Charles River Laboratories International, Wilmington, Mass.) were injected subcutaneously in the flank with a 2004 suspension of $4.0 \times 10^6$ CFPAC-1 cells in 1× PBS. On day 14 after engraftment, mice were injected intravenously with 20 μCi of $^{125}$I-labeled NEO-201 and then necropsied after 1, 2, 4, or 7 days. Blood, tumor tissue, and internal organs (lungs, kidneys, liver, spleen, pancreas, intestines, and stomach) were harvested at each time point (n=4 animals), all tissues were weighed, and radioactivity in tissues was measured using a gamma counter. Data for each mouse was first calculated as cpm/mg tissue, and then tissue cpm values were normalized relative to blood cpm values.

Single-dose Toxicity Study in Cynomolgus Monkeys

A single-dose toxicity study was conducted in purpose-bred cynomolgus monkeys to test NEO-201 for pharmacokinetics and toxicity after a single dose of NEO-201. The duration of the study was 15 days from dose administration, with an additional 14 days quarantine prior to dose administration to acclimate the monkeys to the study room. Eight male and eight female animals (2 animals/sex/group) were dosed by slow intravenous infusion (approximately 30 min±5 min infusion) of NEO-201 diluted in saline solution using an infusion pump and plastic disposable syringe with a catheter extension tubing at dose levels of 0 mg/kg, 5 mg/kg, 20 mg/kg, and 49 mg/kg, which was the highest attainable concentration of antibody. Blood samples were drawn in all animals that received NEO-201 at the following time points: pre-dose, 10 minutes, 1, 2, 4, 6, 24, 48, 72, 96, 168, and 336 hours. Serum was prepared from the blood samples for pharmacokinetic and toxicology analysis. Whole blood was used for cellular analysis. NEO-201 levels in the serum were measured by ELISA using the Human Therapeutic IgG1 ELISA kit (Cayman Chemical, Ann Arbor, Mich.) as per the manufacturer's instructions.

Laboratory tests included hematology and coagulation (baseline (BL), day 2, 8, 15): CBC and differential, activated partial thromboplastin time, fibrinogen and prothrombin time; serum chemistry (BL, day 2, 8, 15): albumin, alkaline phosphatase, ALT, AST, total bilirubin, calcium, total cholesterol, creatine kinase, creatinine, glucose, inorganic phosphorus, total protein, triglyceride, sodium, potassium, chloride, globulin, albumin/globulin ratio, BUN; urinalysis (BL, day 15): color, clarity, glucose, ketones, occult blood, protein, bilirubin, nitrites, pH, urobilinogen, leukocytes, volume, specific gravity; bioanalytical analysis (using ELISA)—(BL, 10 minutes, 1, 2, 4, 6, hours, 24, 48, 72, 96, 168, and 336 hours) from Groups 2 through 4 using Phoenix WinNonlin version 6.1 software (Certara USA, Princeton, N.J.). Animal body weight measurements were recorded (BL, 7, and 14), and neutrophil counts were assessed (BL, day 2, 8, 15).

Statistical Analysis

Data were analyzed using GraphPad Prism (GraphPad Software, La Jolla, Calif.). Comparisons between two groups were conducted by T-test, and p<0.05 was considered statistically significant. Graphs depict the mean±SD from one representative experiment performed in triplicate.

Example 8

ALT-803 Enhances ADCC Mediated by NEO-201

ALT-803 is a novel IL-15 superagonist complex consisting of an IL-15 mutant (IL-15N72D) bound to an IL-15 receptor α/IgG1 Fc fusion protein. This example tests the ability of ALT-803 to modulate ADCC by NEO-201.

Methods

NK cells were isolated from normal donors and were treated with ALT-803 at different concentrations for 48 h prior to be used as effector cells, and human carcinoma cell lines expressing the NEO-201 antigen were utilized as targets in an in vitro non-radioactive ADCC assay. The ability of ALT-803 to affect the phenotype of NK cells and to modulate NK cells gene expression was evaluated by flow cytometry and by using the Nanostring analysis respectively.

Results

Treatment with ALT-803 significantly enhanced the ADCC activity mediated by NEO-201 against NEO-201 positive carcinoma cells (FIG. 8, FIG. 11). The effect of ALT-803 was dose-dependent and achieved statistical significance at all doses tested compared to vehicle control treatment. Treatment of NK cells with ALT-803 enhanced ADCC activity also from donors with minimal ADCC activity and lowered the effective dose of NEO-201 required to initiate the ADCC response compared to untreated NK cells (FIG. 12). Moreover, ADCC activity could be blocked by using anti-CD16 and anti-TIM3 blocking antibodies (FIG. 12).

Phenotypic analysis of NK cells treated with 25 ng/ml of ALT-803 for 48 h demonstrated that ALT-803 enhanced the expression of TIM3 and NKG2D and the mean fluorescence intensity (MFI) of granzyme B and CD107a in CD16/CD56 positive NK cells (FIG. 9).

Nanostring analysis of human NK cells treated with ALT-803 at different concentrations for 48 h showed that ALT-803 was able to modulate mRNA expression of 62 genes (1.6 log₂ fold change compared to vehicle control was considered significant).

ALT-803 treatment up-regulated the mRNA expression of 43 genes, including NK activating receptors, factors involved in the NK cytotoxicity, cytokines and their receptors, and down-regulated the mRNA expression of 19 genes, including NK inhibiting receptors and factors involved in the activation of apoptosis.

Thus, ALT-803 enhances ADCC activity mediated by NEO-201 against human carcinoma cells. The enhancement of the ADCC activity may be in part due to the increase in the expression of TIM3, NKG2D, granzyme B, and CD107a positive NK cells, as well as to the modulation of transcripts that are involved in the NK activation and cytotoxicity.

In summary, treatment of NK cells isolated from normal donors with ALT-803 can enhance the ADCC activity mediated by NEO-201. Phenotypic analysis of ALT-803 treated NK cell isolated from normal donors demonstrated that the ALT-803 can enhance the expression of TIM-3 and NKG2D on CD16/CD56 positive NK cells. Treatment of normal NK cells with ALT-803 can also increase the MFI of granzyme B in CD16/CD56 positive NK cells. Treatment of normal NK cells with ALT-803 can also increase the MFI of CD107a in CD16/CD56 positive NK cells in one of the two donor tested. TIM-3 is an inducible human NK cell receptor that enhances interferon gamma production. It is also a maturation marker. The enhancement of ADCC activity mediated by NEO-201 after treatment with ALT-803 may be in part due to the increased in the expression of TIM-3 positive, NKG2D positive granzyme B positive and CD107a positive NK cells, though this theory is not intended to be limiting. Treatment of NK cells with ALT-803 can enhance the ADCC activity mediated by lower concentrations of NEO-201. Lower concentrations of Mabs can be used to mediate ADCC activity when NK cells were treated with ALT-803 and can generate equivalent levels of cytotoxicity as compare to NK cells without ALT-803 treatment using higher concentration of NEO-201. This result suggests that smaller dose of Mabs may be used in combination with ALT-803 in clinical trials for treatment of cancers.

Example 9

NEO-201 Enhances NK Cell-dependent Killing of Tumor Cells through Blockade of the Inhibitory CEACAM5/CEACAM1 Immune Checkpoint Pathway Immunotherapy using checkpoint blockade antibodies that target effector cell inhibitory receptors, like PD-1 and CTLA-4, have elicited some dramatic and durable responses in several tumor types. Carcinoembryonic antigen-related cell adhesion molecule 1 (CEACAM1) is a cell-surface protein expressed by immune cells and tumor cells, and it can inhibit T cell function similar to PD-1 and CTLA-4. CEACAM1 is also a potent inhibitor of natural killer (NK) cell function; binding between CEACAM1 on NK cells and CEACAM1 or CEACAM5 on tumor cells inhibits activation signaling by NKG2D, which prevents NK cell cytolysis and permits tumor cells to evade NK killing.

NEO-201 binds to members of the CEACAM family, and can activate innate immune mechanisms such as antibody-dependent cellular cytotoxicity (ADCC) and complement-dependent cytotoxicity (CDC) to kill tumor cells. This investigation was designed determine whether NEO-201 blocks the CEACAM1 inhibitory pathway to restore anti-tumor functionality to NK cells.

Methods

In vitro assays using human tumor cell lines were conducted to identify CEACAM family members bound by NEO-201. Functional assays were conducted to assess the ability of NEO-201 to potentiate the in vitro killing of tumor cells by the NK cell line NK-92, which expresses CEACAM1 and lacks CD16 and the ability to mediate ADCC.

Killing assays were performed using a modification of a previously described procedure (David et al., 2017). Briefly, target cells derived from pancreatic (ASPC-1, BxPC-3, CFPAC-1) and colon (LS174T) carcinomas were labeled with 10 µM Calcein AM cell-permeant dye (Thermo Fisher Scientific, Waltham, Mass., USA) for 30 min and then seeded in triplicate at $3.0 \times 10^3$ cells/well into black-walled flat-bottom 96-well culture plates. Tumor cells were then treated with 10 µg/mL of either human IgG1 isotype control antibody (Thermo Fisher Scientific, Waltham, Mass., USA) or NEO-201, and then the natural killer (NK) cell line NK-92 was added at effector-to-target (E:T) ratios of 1.5625:1, 3.125:1, 6.25:1, and 12.5:1. After 16 hr incubation at 37° C., propidium iodide (PI; Thermo Fisher Scientific, Waltham, Mass., USA) was added to each well at a final concentration of 1.67 µg/mL, and the plate was centrifuged, imaged using the Celigo Imaging Cytometer (Nexcelom Bioscence LLC, Lawrence, Mass., USA), and analyzed using GraphPad Prism 7 software (GraphPad Software, La Jolla, Calif.). Live target cells (calcein AM+/PI−) were counted for each well, and specific lysis was calculated as follows: % specific lysis=100−[(average live target count$_{experimental}$/average live target count$_{control}$)×100].

Results

NEO-201 was found to react with distinct variants of CEACAM5 and CEACAM6, but not with CEACAM1 or CEACAM8. Expression profiling revealed that various NEO-201+ cell lines cells expressed differing levels of the native forms of CEACAM5/6 vs. the NEO-201-reactive variant forms of these molecules. Functionally, NEO-201 treatment augmented the cytolytic activity of NK-92 cells against NEO-201+ tumor cells that expressed CEACAM5, but not against NEO-201+ cells that only expressed CEACAM6 (FIG. 13).

Conclusions

NEO-201 reacts with a tumor-associated variant of CEACAM5/6, and can block the interaction between tumor cell CEACAM5 and NK cell CEACAM1 to reverse CEACAM1-dependent inhibition of NK cytotoxicity.

Abbreviations

Antibody-dependent cellular cytotoxicity (ADCC), area under plasma concentration-time curve from time 0 to infinity (AUCinf), dose-normalized area under the plasma concentration-time curve from time 0 to infinity (AUCinf/D), baseline (BL), complement-dependent cytotoxicity (CDC), clearance (CL), maximum observed plasma concentration (Cmax), dose-normalized measured maximum plasma concentration (Cmax/D), estrogen receptor (ER), half-life (HL), immunohistochemistry (IHC), natural killer (NK), non-small cell lung cancer (NSCLC), peripheral blood mononuclear cells (PBMC), progesterone receptor (PR), tumor-associated antigen (TAA), time of maximum observed plasma concentration (Tmax), volume of distribution (Vz).

References

Each document cited herein, including each one in the following list, is hereby incorporated by reference in its entirety.

1. Ferlay J, Soerjomataram I, Dikshit R, Eser S, Mathers C, Rebelo M, Parkin D M, Forman D, Bray F. Cancer incidence and mortality worldwide: sources, methods and major patterns in GLOBOCAN 2012. *Int J Cancer.* 2015 Mar. 1; 136(5):E359-86.
2. Bodey B, Siegel S E, Kaiser H E. Human cancer detection and immunotherapy with conjugated and non-conjugated monoclonal antibodies. *Anticancer Res.* 1996 March-April; 16(2):661-74.

3. Mittal D, Gubin M M, Schreiber R D, Smyth M J. New insights into cancer immunoediting and its three component phases—elimination, equilibrium and escape. Curr Opin Immunol. 2014 April; 27:16-25. doi: 10.1016/j.coi.2014.01.004.
4. Dunn G P, Old L J, Schreiber R D. The three Es of cancer immunoediting. Annu Rev Immunol. 2004; 22:329-60.
5. Carter P. Improving the efficacy of antibody-based cancer therapies. Nat Rev Cancer. 2001 November; 1(2):118-29.
6. Hodge J W, Greiner J W, Tsang K Y, Sabzevari H, Kudo-Saito C, Grosenbach D W, Gulley J L, Arlen P M, Marshall J L, Panicali D, Schlom J. Costimulatory molecules as adjuvants for immunotherapy. Front Biosci. 2006 Jan. 1; 11: 788-803.
7. Vergati M I C, Huen N Y, Schlom J, Tsang K Y. Strategies for cancer vaccine development. J Biomed Biotechnol. 2010; 2010(596432).
8. Gabitzsch E S T K, Palena C, David J M, Fantini M, Kwilas A, Rice A E, Latchman Y, Hodge J W, Gulley J L, Madan R A, Heery C R, Balint J P Jr, Jones F R, Schlom S. The generation and analyses of a novel combination of recombinant adenovirus vaccines targeting three tumor antigens as an immunotherapeutic. Oncotarget. 2015; 6(31):31344-59.
9. Topalian S L, Weiner G J, Pardoll D M. Cancer immunotherapy comes of age. J Clin Oncol. 2011 Dec. 20; 29(36):4828-36.
10. Hollinshead A, Glew D, Bunnag B, Gold P, Herberman R. Skin-reactive soluble antigen from intestinal cancer-cell-membranes and relationship to carcinoembryonic antigens. *Lancet.* 1970; 1(7658):1191-1195.
11. Hollinshead A C, McWright C G, Alford T G D, Gold P, Herbeman R B. Separation of skin reactive intestinal cancer antigen from the carcinoembryonic antigen of Gold. *Science.* 1972; 177(4052):887-889.
12. Hollinshead A, Elias E G, Arlen M, Buda B, Mosley M, Scherrer J. Specific active immunotherapy in patients with adenocarcinoma of the colon utilizing tumor-associated antigens (TAA). A phase I clinical trial. *Cancer.* 1985; 56(3):480-489.
13. Hollinshead A C. Methods of preparing epitopes of tumor associated antigens. U.S. Pat. No. 4,810,781. 1989.
14. Bristol J A, Kantor J A. Recombinant monoclonal antibodies and corresponding antigens for colon and pancreatic cancers. U.S. Pat. No. 7,829,678. 2010.
15. Hollinshead A. Active specific immunotherapy and immunochemotherapy in the treatment of lung and colon cancer. Semin Surg Oncol. 1991 July-August; 7(4):199-210.
16. Luka J, Arlen P M, Bristol A. Development of a serum biomarker assay that differentiates tumor-associated MUC5AC (NPC-1C ANTIGEN) from normal MUC5AC. J Biomed Biotechnol. 2011; 2011:934757. doi: 10.1155/2011/934757. Epub 2010 Dec. 16. PubMed PMID: 21197415
17. Patel S P, Bristol A, Saric O, Wang X P, Dubeykovskiy A, Arlen P M, Morse M A. Anti-tumor activity of a novel monoclonal antibody, NPC-1C, optimized for recognition of tumor antigen MUC5AC variant in preclinical models. Cancer Immunol Immunother. 2013 June; 62(6):1011-9.
18. Beg M S, Azad N S, Patel S P, Torrealba J, Mavroukakis S, Beatson M A, Wang X P, Arlen P M, Morse M A. A phase 1 dose-escalation study of NEO-102 in patients with refractory colon and pancreatic cancer. Cancer Chemother Pharmacol. 2016 September; 78(3):577-84.
19. Kim R D, Arlen P M, Tsang K Y, Mavroukakis S A, Zaki A, Cui K, Azad N S, Tan Jr. B R, Poplin E, Morse M A, Beg M S. Ensituximab (E) in patients (pts) with refractory metastatic colorectal cancer (mCRC): Results of a phase ½ clinical trial. J Clin Oncol 35, 2017 (suppi; abstr 3081).
20. Zeligs K, Arlen P M, Tsang K, Hernandez L, Fantini M, Annunziata C M. Abstract 3025: Preclinical characterization of a novel monoclonal antibody targeting a neo-antigen expressed in ovarian and GI malignancies. Cancer Res Jul. 1 2017 (77) (13 Supplement) 3025.
21. Seidel U J, Schlegel P, Lang P. Natural killer cell mediated antibody-dependent cellular cytotoxicity in tumor immunotherapy with therapeutic antibodies. *Front Immunol.* 2013 March, 27; 4:76.
22. Petricevic B, Laengle J, Singer J, Sachet M, Fazekas J, Steger G, Bartsch R, Jensen-Jarolim E, Bergmann M. Trastuzumab mediates antibody-dependent cell-mediated cytotoxicity and phagocytosis to the same extent in both adjuvant and metastatic HER2/neu breast cancer patients. *J Transl Med.* 2013 Dec. 12; 11:307.
23. Dall'Ozzo S, Tartas S, Paintaud G, Cartron G, Colombat P, Bardos P, Watier H, Thibault G. Rituximab-dependent cytotoxicity by natural killer cells: influence of FCGR3A polymorphism on the concentration-effect relationship. *Cancer Res.* 2004 Jul. 1; 64(13):4664-9.
24. Levy E M, Sycz G, Arriaga J M, Barrio M M, von Euw E M, Morales S B, González M, Mordoh J, Bianchini M. Cetuximab-mediated cellular cytotoxicity is inhibited by HLA-E membrane expression in colon cancer cells. *Innate Immun.* 2009 April; 15(2):91-100.
25. Kawaguchi Y, Kona K, Mimura K, Sugai H, Akaike H, Fujii H. Cetuximab induce antibody-dependent cellular cytotoxicity against EGFR-expressing esophageal squamous cell carcinoma. *Int J Cancer.* 2007 Feb. 15; 120 (4):781-7.
26. López-Albaitero A, Lee S C, Morgan S, Grandis J R, Gooding W E, Ferrone S, Ferris R L. Role of polymorphic Fc gamma receptor IIIa and EGFR expression level in cetuximab mediated, NK cell dependent in vitro cytotoxicity of head and neck squamous cell carcinoma cells. *Cancer Immunol Immunother.* 2009 November; 58 (11): 1853-64. doi: 10.1007/s00262-009-0697-4.
27. Boyerinas B, Jochems C, Fantini M, Heery C R, Gulley J L, Tsang K Y, Schlom J. Antibody-Dependent Cellular Cytotoxicity Activity of a Novel Anti-PD-L1 Antibody Avelumab (MSB0010718C) on Human Tumor Cells. Cancer Immunol Res. 2015 October; 3(10):1148-57.
28. Meyer S, Leusen J H, Boross P. Regulation of complement and modulation of its activity in monoclonal antibody therapy of cancer. MAbs. 2014; 6(5):1133-44.
29. Strome S E, Sausville E A, Mann D. A mechanistic perspective of monoclonal antibodies in cancer therapy beyond target-related effects. Oncologist. 2007 September; 12(9):1084-95.
30. Hayes J, Frostell A, Karlsson R, Miller S, Millan-Martin S, Pauers M, Reuss F, Cosgrave E, Anneren C, Davey G P, Rudd P M. Identification of Fc gamma receptor glycoforms that produce differential binding kinetics for rituximab. Mol Cell Proteomics. 2017 June 2. pii: mcp.M117.066944. doi: 10.1074/mcp.M117.066944. [Epub ahead of print]
31. Koene H R, Kleijer M, Algra J, Roos D, von dem Borne A E, de Haas M. Fc gammaRIIIa-158V/F polymorphism influences the binding of IgG by natural killer cell Fc gammaRIIIa, independently of the Fc gammaRIIIa-48L/R/H phenotype. Blood. 1997 Aug. 1; 90(3):1109-14. PubMed PMID: 9242542.
32. Wu J, Edberg J C, Redecha P B, Bansal V, Guyre P M, Coleman K, Salmon J E, Kimberly R P. A novel polymorphism of FcgammaRIIIa (CD16) alters receptor function and predisposes to autoimmune disease. J Clin Invest. 1997 Sep. 1; 100(5):1059-70. PubMed PMID: 9276722

33. Musolino A, Naldi N, Bortesi B, Pezzuolo D, Capelletti M, Missale G, Laccabue D, Zerbini A, Camisa R, Bisagni G, Neri T M, Ardizzoni A. Immunoglobulin G fragment C receptor polymorphisms and clinical efficacy of trastuzumab-based therapy in patients with HER-2/neu-positive metastatic breast cancer. J Clin Oncol. 2008 Apr. 10; 26(11):1789-96.

34. Hank J A, Robinson R R, Surfus J, Mueller B M, Reisfeld R A, Cheung N K, Sondel P M. Augmentation of antibody dependent cell mediated cytotoxicity following in vivo therapy with recombinant interleukin 2. Cancer Res. 1990 Sep. 1; 50(17):5234-9.

35. Watanabe M, Kono K, Kawaguchi Y, Mizukarni Y, Mimura K, Maruyama T, Fujii H. Interleukin-21 can efficiently restore impaired antibody-dependent cell-mediated cytotoxicity in patients with oesophageal squamous cell carcinoma. Br J Cancer. 2010 Feb. 2; 102(3): 520-9.

36. Han K P, Zhu X, Liu B, Jeng E, Kong L, Yovandich J L, Vyas V V, Marcus W D, Chavaillaz P A, Romero C A, Rhode P R, Wong H C. IL-15:IL-15 receptor alpha superagonist complex: high-level co-expression in recombinant mammalian cells, purification and characterization. Cytokine. 2011 December; 56(3):804-10.

37. Gomes-Giacoia E, Miyake M, Goodison S, Sriharan A, Zhang G, You L, Egan J O, Rhode P R, Parker A S, Chai K X, Wong H C, Rosser C J. Intravesical ALT-803 and BCG treatment reduces tumor burden in a carcinogen induced bladder cancer rat model; a role for cytokine production and NK cell expansion. PLoS One. 2014 Jun. 4; 9(6):e96705.

38. Mathios D, Park C K, Marcus W D, Alter S, Rhode P R, Jeng E K, Wong H C, Pardoll D M, Lim M. Therapeutic administration of IL-15 superagonist complex ALT-803 leads to long-term survival and durable antitumor immune response in a murine glioblastoma model. Int J Cancer. 2016 Jan. 1; 138(1):187-94.

39. Rhode P R, Egan J O, Xu W, Hong H, Webb G M, Chen X, Liu B, Zhu X, Wen J, You L, Kong L, Edwards A C, Han K, Shi S, Alter S, Sacha J B, Jeng E K, Cai W, Wong H C. Comparison of the Superagonist Complex, ALT-803, to IL15 as Cancer Immunotherapeutics in Animal Models. Cancer Immunol Res. 2016 January; 4(1):49-60.

40. Kim P S, Kwilas A R, Xu W, Alter S, Jeng E K, Wong H C, Schlom J, Hodge J W. IL-15 superagonist/IL-15RαSushi-Fc fusion complex (IL-15SA/IL-15RαSu-Fc; ALT-803) markedly enhances specific subpopulations of NK and memory CD8+ T cells, and mediates potent anti-tumor activity against murine breast and colon carcinomas. Oncotarget. 2016 Mar. 29; 7(13):16130-45.

41. Felices M, Chu S, Kodal B, Bendzick L, Ryan C, Lenvik A J, Boylan K L M, Wong H C, Skubitz A P N, Miller J S, Geller M A. IL-15 super-agonist (ALT-803) enhances natural killer (NK) cell function against ovarian cancer. Gynecol Oncol. 2017 June; 145(3):453-461.

42. Rosario M, Liu B, Kong L, Collins L I, Schneider S E, Chen X, Han K, Jeng E K, Rhode P R, Leong J W, Schappe T, Jewell B A, Keppel C R, Shah K, Hess B, Romee R, Piwnica-Worms D R, Cashen A F, Bartlett N L, Wong H C, Fehniger T A. The IL-15-Based ALT-803 Complex Enhances FcγRIIIa-Triggered NK Cell Responses and In Vivo Clearance of B Cell Lymphomas. Clin Cancer Res. 2016 Feb. 1; 22(3):596-608.

43. Seya T, Matsumoto M, Hara T, Hatanaka M, Masaoka T, Akedo H. Distribution of C3-step regulatory proteins of the complement system, CD35 (CR1), CD46 (MCP), and CD55 (DAF), in hematological malignancies. Leuk Lymphoma. 1994 February; 12(5-6):395-400.

44. Niehans G A, Cherwitz D L, Staley N A, Knapp D J, Dalmasso A R Human carcinomas variably express the complement inhibitory proteins CD46 (membrane cofactor protein), CD55 (decay-accelerating factor), and CD59 (protectin). Am J Pathol. 1996 July; 149(1):129-42.

45. Donin N, Jurianz K, Ziporen L, Schultz S, Kirschfink M, Fishelson Z. Complement resistance of human carcinoma cells depends on membrane regulatory proteins, protein kinases and sialic acid. Clin Exp Immunol. 2003 February; 131(2):254-63.

46. Hsu Y F, Ajona D, Corrales L, Lopez-Picazo J M, Gurpide A, Montuenga L M, Pio R. Complement activation mediates cetuximab inhibition of non-small cell lung cancer tumor growth in vivo. Mol Cancer. 2010 Jun. 7; 9:139.

47. Konishi E, Kitai Y, Kondo T. Utilization of complement-dependent cytotoxicity to measure low levels of antibodies: application to nonstructural protein 1 in a model of Japanese encephalitis virus. Clin Vaccine Immunol. 2008 January; 15(1):88-94.

48. David J M, Dominguez C, McCampbell K K, Gulley J L, Schlom J, Palena C. A novel bifunctional anti-PD-L1/TGF-β Trap fusion protein (M7824) efficiently reverts mesenchymalization of human lung cancer cells. OncoImmunology. 2017 Jul. 13; 6(10):e1349589.

TABLE 1

Flow cytometry analysis of NEO-201 binding to cultured tumor cell lines derived from various types of solid tumors. The percentage of positive cells and mean fluorescence intensity (MFI) values are detailed for each cell line. NEO-201 positive cell lines appear in bold text. NEO-201 positivity was defined as % positive >10%.

| CELL LINE | TUMOR TYPE | % POSITIVE | MFI |
| --- | --- | --- | --- |
| COLO 205 | Colon | 10.33 | 245 |
| HT-29 | Colon | 38.40 | 352 |
| LS174T | Colon | 46.46 | 345 |
| SW1116 | Colon | 2.36 | 194 |
| SW1463 | Colon | 1.23 | 278 |
| SW480 | Colon | 1.70 | 575 |
| ASPC-1 | Pancreatic | 79.26 | 8927 |
| BxPC-3 | Pancreatic | 97.25 | 2584 |
| CAPAN-2 | Pancreatic | 29.69 | 327 |
| CFPAC-1 | Pancreatic | 97.79 | 9281 |
| PANC-1 | Pancreatic | 3.29 | 289 |
| H441 | NSCLC (adenocarcinoma) | 69.16 | 675 |
| H522 | NSCLC (adenocarcinoma) | 1.38 | 238 |
| HCC4006 | NSCLC (adenocarcinoma) | 99.27 | 9899 |
| HCC827 | NSCLC (adenocarcinoma) | 77.46 | 692 |
| SK-LU-1 | NSCLC (adenocarcinoma) | 1.77 | 685 |
| CALU-1 | NSCLC (squamous) | 4.22 | 571 |
| H1703 | NSCLC (squamous) | 4.16 | 111 |
| H226 | NSCLC (squamous) | 4.83 | 209 |
| H520 | NSCLC (squamous) | 61.78 | 443 |
| AU-565 | Breast (HER2+) | 50.04 | 227 |
| BT-474 | Breast (PR+/HER2+) | 68.79 | 591 |
| HCC1500 | Breast (ER+/PR+) | 1.53 | 597 |
| SK-BR-3 | Breast (HER2+) | 1.61 | 329 |
| T-47D | Breast (ER+/PR+) | 8.00 | 161 |
| ZR-75-1 | Breast (ER+/PR+/HER2+) | 68.80 | 550 |
| BT-549 | Breast (ER−/PR−/HER2−) | 1.47 | 477 |
| HCC1937 | Breast (ER−/PR−/HER2−) | 19.14 | 510 |
| HCC38 | Breast (ER−/PR−/HER2−) | 2.15 | 226 |
| MDA-MB-468 | Breast (ER−/PR−/HER2−) | 6.33 | 344 |

TABLE 2

IHC profile of NEO-201 staining of normal human microarray tissues.

| TISSUE TYPE | POSITIVE/TOTAL |
|---|---|
| Cerebral Cortex | 0/2 |
| Cerebellum | 0/2 |
| Basal Ganglia | 0/2 |
| Hippocampus | 0/2 |
| Spinal Cord | 0/2 |
| Heart | 0/2 |
| Lung | 0/2 |
| Bronchus | 0/2 |
| Tongue | 2/2, weak |
| Esophagus | 0/2 |
| Stomach | 0/2 |
| Breast | 0/2 |
| Liver | 0/2 |
| Prostate | 0/2 |
| Testis | 0/2 |
| Ovary | 0/2 |
| Fallopian Tube | 0/2 |
| Spleen | 0/2 |
| Lymph node | 0/2 |
| Tonsil | 0/2 |
| Thymus | 0/2 |
| Paratoid gland | 0/2 |
| Skeletal muscle | 0/2 |
| Ureter | 0/2 |
| Exocervix | 2/2, weak |
| Endocervix | 0/2 |
| Pro-endometrium | 0/2 |
| Sec-endometrium | 0/2 |
| Myometrium | 0/2 |
| Umbilical cord | 0/2 |
| Soft Tissue | 0/2 |
| Placenta:amnion | 0/2 |
| Placenta; chorionvilli | 0/2 |
| Placenta; basal plate | 0/2 |

Table 3: Pharmacokinetic results of single-dose NEO-201 administration in cynomolgus monkeys. Eight male and eight female animals (2 animals/sex/group) were injected intravenously with 0 mg/kg (saline solution) or 5 mg/kg, 20 mg/kg, or 49 mg/kg of NEO-201. Blood samples were drawn in all animals that received NEO-201 at various time points (pre-dose, 10 min, 1, 2, 4, 6, 24, 48, 72, 96, 168, and 336 hr post dose), and pharmacokinetic measurements from serum preparations were obtained by ELISA. Values in the table represent the average from the 2 animals/sex/group (M, F) or from all 4 animals (All).

Abbreviations: area under plasma concentration-time curve from time 0 to infinity (AUCinf); dose-normalized area under the plasma concentration-time curve from time 0 to infinity (AUCinf/D); clearance (CL); maximum observed plasma concentration (Cmax); dose-normalized measured maximum plasma concentration (Cmax/D); half-life (HL); time of maximum observed plasma concentration (Tmax); volume of distribution (Vz).

| Dose Level | Sex | HL (hr) | Tmax (hr) | Cmax (µg/mL) | Cmax/D (µg/mL/mg) | AUCinf (hr × µg/mL) | AUCinf/D (hr × µg/mL/mg) | CL (mL/hr) | Vz (mL) |
|---|---|---|---|---|---|---|---|---|---|
| 5 mg/kg | M | 58.5 | 0.584 | 135 | 10.4 | 8,210 | 640 | 1.67 | 137 |
|  | F | 34.0 | 0.584 | 142 | 12.4 | 8,230 | 720 | 1.41 | 69.8 |
|  | All | 46.2 | 0.584 | 138 | 11.4 | 8,220 | 680 | 1.54 | 103 |
| 20 mg/kg | M | 176 | 0.167 | 639 | 12.3 | 77,600 | 1,500 | 0.669 | 171 |
|  | F | 158 | 0.167 | 518 | 10.1 | 62,700 | 1,230 | 0.823 | 187 |
|  | All | 167 | 0.167 | 579 | 11.2 | 70,100 | 1,360 | 0.746 | 179 |
| 49 mg/kg | M | 122 | 0.167 | 1,460 | 11.6 | 126,000 | 1,000 | 1.00 | 174 |
|  | F | 219 | 0.167 | 1,470 | 11.9 | 187,000 | 1,520 | 0.658 | 208 |
|  | All | 170 | 0.167 | 1,470 | 11.8 | 157,000 | 1,260 | 0.830 | 191 |

The invention claimed is:

1. A method of promoting antibody-dependent cell-mediated cytotoxicity (ADCC) or natural killer (NK) cell-mediated killing of carcinoma cells which express a CEACAM antigen bound by the NEO-201 antibody in a patient in need thereof consisting essentially of administering:
  (i) a NEO-201 antibody to said patient in need thereof, wherein said NEO-201 antibody comprises a heavy chain wherein the CDR1 comprises the amino acid sequence of SEQ ID NO: 32, the CDR2 comprises the amino acid sequence of SEQ ID NO: 33, and the CDR3 comprises the amino acid sequence of SEQ ID NO: 34; and comprises a light chain wherein the CDR1 comprises the amino acid sequence of SEQ ID NO: 35, the CDR2 comprises the amino acid sequence of SEQ ID NO: 36, and the CDR3 comprises the amino acid sequence of SEQ ID NO: 37; and
  (ii) an IL-15 agonist or an IL-15 superagonist, wherein said moieties (i) and (ii) are administered separately or in combination, under conditions whereby the IL-15 agonist or the IL-15 superagonist enhances ADCC or NK cell-mediated killing of carcinoma cells by the NEO-201 antibody in said patient compared to the amount of ADCC or NK cell-mediated killing of carcinoma cells if the same dose of NEO-201 antibody is administered in the absence of said IL-15 agonist or an IL-15 superagonist; and
  wherein said patient is natural killer (NK)-depleted prior to or at the time of said administering; and/or said patient is severely NK-depleted prior to or at the time of said administering.

2. The method of claim 1, further comprising, prior to or at the time of said administering, determining whether said patient is NK-depleted or is severely NK-depleted.

3. The method of claim 1, wherein (a) said patient who is NK-depleted has a NK cell deficiency (NKD), optionally comprising CNKD-, or FNKD-; (b) said patient who is NK-depleted is NK-depleted or severely NK-depleted as a result of another therapy; (c) said patient who is NK-depleted is undergoing a cancer therapy; (d) said patient who is NK-depleted is undergoing chemotherapy or radiotherapy, wherein optionally said chemotherapy comprises administration of one or more proteasome inhibitors-, Histone deacetylase inhibitors-, genotoxic agents-, GSK inhibitors-, BET inhibitors-, HSP90 inhibitors-, microtubule assembly inhibitors-, and/or immunomodulatory drugs.

4. The method of claim 1, wherein said patient who is NK-depleted prior to or at the time of said administering, (a) NK cells comprise less than 5% of the peripheral blood mononuclear cells (PBMCs) in said individual; (b) NK cells comprise less than 3% of the peripheral blood mononuclear cells (PBMCs) in said individual; (c) less than 70% of PBMC NK cells in said patient are CD56dimCD16+NK cells; and/or (d) less than 50% of PBMC NK cells in said patient are CD56dimCD16+NK cells.

5. The method of claim 1, wherein said NEO-201 antibody comprises:
  a variable heavy chain sequence having at least 90% identity to SEQ ID NO: 38 and a variable light chain sequence having at least 90% identity to SEQ ID NO: 39; or
  the variable heavy chain sequence of SEQ ID NO: 38 and the variable light chain of SEQ ID NO: 39.

6. The method of claim 1, wherein said NEO-201 antibody: (a) comprises a human IgG1 constant domain; and/or (b) is humanized.

7. The method of claim 1, wherein (said IL-15 agonist comprises ALT-803.

8. The method of claim 1, wherein the minimum effective dosage of said NEO-201 antibody that provides for killing of carcinoma cells in the patient is reduced compared to the minimum effective dosage of the NEO-201 antibody that provides for killing of carcinoma cells in the patient in the absence of said IL-15 agonist or IL-15 superagonist.

9. The method of claim 1, wherein said cancer comprises colon cancer.

10. The method of claim 1, wherein said cancer comprises pancreatic cancer.

11. The method of claim 1, wherein said cancer comprises ovarian cancer.

12. The method of claim 1, wherein said cancer comprises stomach cancer.

13. The method of claim 1, wherein said cancer comprises lung cancer.

14. The method of claim 1, wherein said cancer comprises breast cancer.

15. The method of claim 1, wherein said cancer comprises uterine cancer.

16. The method of claim 1, wherein said IL-15 agonist or superagonist is administered prior to the NEO-201 antibody.

17. The method of claim 1, wherein said IL-15 agonist or superagonist is administered concurrent to the NEO-201 antibody.

18. The method of claim 1, wherein said IL-15 agonist or superagonist results in enhanced expression of TIM3 and NKG2D by NK cells in the patient.

19. The method of claim 17, wherein said IL-15 agonist or superagonist is ALT-803.

\* \* \* \* \*